US010011602B2

(12) United States Patent
Kjer-Nielsen et al.

(10) Patent No.: US 10,011,602 B2
(45) Date of Patent: Jul. 3, 2018

(54) IMMUNOLOGICAL REAGENTS AND USES THEREFOR

(71) Applicants: THE UNIVERSITY OF MELBOURNE, Carlton, Victoria (AU); MONASH UNIVERSITY, Clayton, Victoria (AU); THE UNIVERSITY OF QUEENSLAND, St. Lucia, Queensland (AU)

(72) Inventors: Lars Kjer-Nielsen, Carlton (AU); James McCluskey, Carlton (AU); Alexandra Corbett, Carlton (AU); Jamie Rossjohn, Clayton (AU); Patel Onisha, Clayton (AU); David Paul Fairlie, Brisbane (AU); Ligong Liu, Brisbane (AU)

(73) Assignee: THE UNIVERSITY OF MELBOURNE, Carlton (AU)

( * ) Notice: Subject to any disclaimer, the term of this patent is extended or adjusted under 35 U.S.C. 154(b) by 222 days.

(21) Appl. No.: 14/413,164

(22) PCT Filed: Jul. 5, 2013

(86) PCT No.: PCT/AU2013/000742
§ 371 (c)(1),
(2) Date: Jan. 6, 2015

(87) PCT Pub. No.: WO2014/005194
PCT Pub. Date: Jan. 9, 2014

(65) Prior Publication Data

US 2015/0166542 A1 Jun. 18, 2015

(30) Foreign Application Priority Data

Jul. 6, 2012 (AU) ................................ 2012902899
Aug. 10, 2012 (AU) ................................ 2012903446
Oct. 8, 2012 (AU) ................................ 2012904386
Jun. 20, 2013 (AU) ................................ 2013902246

(51) Int. Cl.
*C07D 475/02* (2006.01)
*C07D 475/04* (2006.01)
*G01N 33/50* (2006.01)
*A61K 38/17* (2006.01)
*C07K 14/74* (2006.01)
*C12N 5/0783* (2010.01)
*G01N 33/569* (2006.01)

(52) U.S. Cl.
CPC ........ *C07D 475/04* (2013.01); *A61K 38/1774* (2013.01); *C07D 475/02* (2013.01); *C07K 14/70539* (2013.01); *C12N 5/0636* (2013.01); *G01N 33/505* (2013.01); *G01N 33/56972* (2013.01); *C07K 2299/00* (2013.01); *C12N 2500/46* (2013.01); *G01N 2333/70539* (2013.01)

(58) Field of Classification Search
None
See application file for complete search history.

(56) References Cited

U.S. PATENT DOCUMENTS 3,445,336 A * 5/1969 Nakamura .............. C12P 25/00
435/840

FOREIGN PATENT DOCUMENTS

WO 2003/095606 A2 11/2003

OTHER PUBLICATIONS

Le Bourhis (Nature Immunology Aug. 2010 11(8): 701-709.*
Huang et al. (J. Exp. Med. Apr. 28, 2008 205(5): 1201-1211, the abstract, in particular).*
Kjer-Nielsen et al. (Nature Oct. 10, 2012 491: 717-725, p. 717—right column, in particular).*
Huang, S. et al., "Evidence for MR1 Antigen Presentation to Mucosal-associated Invariant T Cells," J. Biol. Chem., 2005, 280(22), 21183-21193.

* cited by examiner

*Primary Examiner* — Peter J Reddig
(74) *Attorney, Agent, or Firm* — McCarter & English, LLP; Marie Laccotripe Zacharakis; Joshua J. Galgano

(57) ABSTRACT

The present invention provides a ligand which binds to MR1 wherein said binding results in binding of the MR1 to MAIT cells.

11 Claims, 2 Drawing Sheets

IMMUNOLOGICAL REAGENTS AND USES THEREFOR

RELATED APPLICATIONS

This application is a 35 U.S.C. § 371 national stage filing of International Application No. PCT/AU2013/000742, filed Jul. 5, 2013, which claims priority to Australian Patent Application No. 2012902899, filed Jul. 6, 2012, Australian Patent Application No. 2012903446, filed Aug. 10, 2012, Australian Patent Application No. 2012904386, filed Oct. 8, 2012 and Australian Patent Application No. 2013902246, filed Jun. 20, 2013. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Dec. 17, 2014, is named Sequence_Listing.txt and is 12,502 bytes in size.

FIELD OF THE INVENTION

The present invention relates generally to the field of immunology, including the detection and monitoring of components in the immune system and immunotherapeutic protocols. Immunological reagents are provided which are useful in determining the state of the adaptive cellular immune response system in a subject.

DESCRIPTION OF THE PRIOR ART

The reference to any prior art in this specification is not, and should not be taken as, an acknowledgment or any form of suggestion that that prior art forms part of the common general knowledge in Australia or elsewhere.

Bibliographic details of the publications referred to by author in this specification are collected at the end of the description.

Cellular immune responses are often initiated by T cells bearing αβ-T cell receptors (TCRs) which typically recognize foreign virally derived peptides bound to classical major histocompatibility complex (MHC) molecules on specialized antigen presenting cells (Zinkernagel and Doherty, 1997). There are two classes of MHC molecules—MHC class I (MHC-I) and MHC class II (MHC-II). Within MHC-I, there are two subclasses, MHC-Ia ('classical' MHC) and MHC-Ib ('non-classical' MHC).

Major histocompatibility complex-related protein 1 (MR1) is a MHC class 1b molecule encoded by a single functional, monomorphic Mr1 gene in antigen presenting cells. The MR1 protein, like MHC class I, is comprised of a heavy chain (comprised of the α1, α2 and α3 domains) non-covalently associated with a light chain (β2-microglobulin). The Mr1 gene is not Mhc linked, is highly conserved, and seems to be unique to mammals. As striking evidence for interspecies conservation, the predicted amino acid sequences of mouse MR1 (mMR1) and human MR1 are 89/90% identical in their α1/α2 domains. By contrast, mouse and human MHC-linked class Ia and Ib molecules are 69/70% and 51/41% identical, respectively. The high level of polymorphism of classical MHC molecules allows them to present diverse peptides to T cells during the adaptive immune response to pathogens. By contrast, the remarkable conservation of MR1 suggests that it evolved under strong negative selection, possibly imposed by immune responses to pathogens. MR1 message and protein are ubiquitously expressed in different tissues. Endogenous MR1 is only detected on the plasma membrane of cells from murine or human origins at very low levels using available mAbs considered specific for MR1. However, higher levels of surface expression of MR1 can be achieved using transfection or transduction to overexpress an MR1-encoding cDNA in mouse or human cell lines. The failure to detect even moderate levels of endogenous MR1 at the cell surface is suggested to reflect limited ligand supply as is the case with the non-classical MHC, H2-M3, which presents N-formylated peptides.

MR1 expression is required for the in vivo development of a novel population of T cells which are typically classified as possessing an invariant TCRα-chain (i.e. identical Vα-Jα combination). Based on quantitative PCR analysis, these invariant T cells were found to preferentially reside in the lamina propria of the intestine and the lung in mice and humans. Thus, they were assigned the acronym MAIT (mucosal-associated invariant T) cells.

The importance of the role of MAIT cells in immunity is indicated by their conservation across species such as humans, cattle and mice, as well as recent data implying protective function in certain infections (Gold et al., 2010a; Le Bourhis et al., 2011; Le Bourhis et al., 2010) and inflammatory conditions including multiple sclerosis. In humans, MAIT cells comprise 1-10% of peripheral blood T cells when compared to their NKT cell counterparts (typically less than 0.1%) (Godfrey et al., 2010b). Indeed, MAIT cells are found in human blood, the gastrointestinal mucosa and mesenteric lymph nodes. Furthermore, MAIT cells, like NKT cells, rapidly produce a broad range of cytokines upon activation (Kawachi et al., 2006; Martin et al., 2009). There are further parallels between MR1-restricted MAIT cells and CD1d-restricted NKT cells in that, like NKT cells, MAIT cells typically express a semi-invariant TCR, comprised of an invariant TCR alpha-chain (Vα19Jα33 in mice or the homologous Vα7.2Jα33 in humans) in combination with TCR-Vβ6 or Vβ8 in mice and TCR-Vβ2 or Vβ13 in humans. The semi-invariant and evolutionarily conserved nature of the MAIT TCR suggests that MAIT cells are specific for an important, albeit limited and atypical, class of antigens (Ags) presented by the MR1 molecule. Further, evidence for a highly conserved MAIT-ligand comes from mutagenesis studies of MAIT TCRs with different Vβ-segments which have revealed that a defined cluster of amino acid residues are crucial for MAIT cell recognition of diverse microbes (Reantragoon et al, 2012). MAIT cells respond to a surprisingly broad range of microorganisms, excluding viruses but including diverse strains of bacteria and yeast, suggesting the existence of a conserved Ag (or family of Ag), common to these cellular organisms, presented to MAIT cells in an MR1-dependent manner (Gold et al., 2010a; Gold et al., 2010b; Le Bourhis et al., 2010). This suggests a much broader role in the immune response than is indicated by their limited TCR repertoire.

The MAIT cell subpopulation has been found to infiltrate diseased organs in various illnesses including bacterial infection, kidney and brain tumors (Peterfalvi et al. 2008), as well as Multiple Sclerosis (MS).

In humans, MAIT cells are defined as $CD161^{hi}$, IL-18Rα, $^{+}V\alpha7.2^{+}$, $\gamma\delta^{-}CD3^{+}$ lymphocytes. Current methods of staining of MAIT cells in both peripheral blood and tissues require either staining for CD161 or IL-18Rα expression at the cell surface, together with staining of the Vα7.2 segment (Martin et al, 2009; Le Bourhis et al, 2010). A key limitation of this phenotypic characterization of MAIT cells is that these cells may include T cells other than those expressing the Vα7.2. Moreover, T cells that do express the Vα7.2 also occur in the normal course of other immune responses including MHC-restricted responses and potentially other MHC 1b-restricted immunity and therefore these Vα7.2$^+$ cells are unrelated to MAIT cell specificity. Hence, the monitoring and identification of MAIT cells by current techniques reliant entirely on a Vα7.2 phenotype is subject to a significant 'false-positive' effect.

Because of the emerging importance of the role that MAIT cells play in the immune response, there is a need to identify the exact mechanisms by which MAIT cells exert their protective effects. This has been significantly hindered since hithertofore the precise identity of the MR1-restricted Ag(s) which represents a key step in understanding MAIT cell biology has been unknown.

Thus, there remains a need to identify the ligand(s) bound by MR1, including determining the TCR antigen specificity of MAIT cells.

SUMMARY OF THE INVENTION

The present invention is predicted in part on the identification of MAIT cell restricted antigens which interact with MR1. This has enabled the manipulation of MR1-antigen subunits and multimeric complexes to facilitate the detection and state of stimulation of MAIT cells. The ability to ascertain MAIT cell presence and level of stimulation facilitates an assessment of the state of the adaptive cellular immune response system in a subject.

The present specification teaches methods and immunological reagents useful for labeling MAIT cells. Enabled herein are MR1-ligand subunits and stable multimeric complexes comprising same. The MR1-ligand subunit and complexes comprising same are recognised by T-cell receptors (TCRs) on MAIT cells, thereby allowing for the labeling, identification, separation and characterisation of MAIT cells. The subject immunological reagents are also useful for the diagnosis and monitoring of diseases have a cellular immune response component. The present invention enables development of methods of MAIT cell detection for both research and diagnostic purposes within the field of immunology as well as the development of therapeutic methods for the treatment or prevention of conditions associated with aberrant MAIT cell activity.

For the purposes of the present invention, the MR1 receptor on an antigen presenting cell or in soluble form comprises an α heavy chain comprising domains α1, α2 and α3 and a β2-microglobulin light chain.

The monomeric form of MR1 (i.e. a single MR1) is referred to herein as an "MR1 subunit" and is represented by [MR1].

When a ligand is bound to MR1, this is represented as:

[MR1-L]

MR1 is as defined as above; and L is a ligand including a naturally occurring antigen or an artificially created ligand.

MR1 can form multimeric structures facilitated by a multi-valence binding molecule. Hence, the formula:

$[MR1]_n$ means a complex of two or more MR1 subunits up to n, which is the valence number of the multi-valence binding molecule.

When the MR1 subunit is bound with a ligand, and it is in multimeric form, it is represented as:

$[MR1\text{-}L]_n$

It is proposed herein the MR1 subunit ([MR1]), MR1 multimeric complexes ($[MR1]_n$), MR1-ligand subunit ([MR1-L]) and MR1-ligand multimeric complexes ($[MR1\text{-}L]_n$) are useful in the binding, detection, stimulation and monitoring of MAIT cells in soluble form or as part of an antigen presenting cell. Depending on the ligand, soluble or cell found [MR1-L] subunits or multimeric complexes can have an agonistic or antagonistic role in MAIT cell stimulation.

The present invention, therefore, provides an MR1 subunit or multimeric form thereof which is useful in the detection and monitoring of MAIT cells and in modulating MAIT cell activity. The MR1 subunit or multimeric forms thereof may also comprise a ligand. In an embodiment, the ligand is an antigen.

Reference to a "ligand" (L) includes an antigen or agent which binds to MR1 resulting in binding to MAIT cells and optionally, resulting in the stimulation or inhibition of the MAIT cells via MAIT cell TCR. A ligand may be proteinacous or non-proteinacous in nature and includes analogs and derivatives of naturally occurring antigens which retain the ability to bind to MR1 or which enable refolding of MR1 into its native form.

In an embodiment the ligand is represented by formula (I):

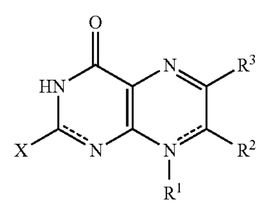

(I)

wherein:

X is selected from the list consisting of hydroxyl, oxo, amino, mono-$C_1$-$C_3$alkylamino or di-$C_1$-$C_3$alkylamino;

$R^1$ is present or absent and is selected from the list consisting of hydrogen, optionally substituted aryl, optionally substituted heteroaryl, and optionally substituted $C_1$-$C_{10}$alkyl;

$R^2$ and $R^3$ are each independently selected from the list consisting of hydrogen, halogen, halo $C_1$-$C_3$alkyl, optionally substituted $C_1$-$C_3$alkoxy, optionally substituted aryl, optionally substituted heteroaryl, and optionally substituted $C_1$-$C_3$alkyl; and --- represents an optional double bond;

or a pharmaceutically acceptable salt, solvate, or hydrate thereof, or a tautomer or stereoisomer thereof, in any isomeric ratio, including racemates and enantiomerically enriched mixtures.

With reference to formula (I), the optional substituents include but are not limited to a group selected from the list consisting of halogen, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4alkyl)_2$, —CN, —$NO_2$, mercapto, —$S(O_2)NH_2$, —$S(O_2)NHC_1$-$C_4$alkyl and $CO_2H$.

In an embodiment, the ligand interacts with MR1 and acts as an antagonist of mammalian MAIT cells, including human and rodent MAIT cells. In an embodiment the ligand is 6-formyl pterin, or a functional analog or derivative thereof. A non-limiting example of a functional analog of 6-formyl pterin is acetyl 6-formyl pterin.

In an embodiment, the ligand interacts with MR1 and activates mammalian MAIT cells including human and rodent MAIT cells. In an embodiment, the ligand is a compound selected from the list consisting of rRL-6-HM (also known interchangeably as rRL-6-$CH_2OH$). rRL-6AM, rRL-6HM, RL-6M, RP-5PA, 6-methyl-7-hydroxy-8-ribityl lumazine, 6-,7-dimethyl-8-ribityl lumazine or a functional analog of any one thereof, including but not limited to oxidised and reduced forms thereof. In an embodiment, the ligand is rRL-6-HM.

In an embodiment the present invention provides multimeric complexes of MR1 bound to the ligand. In this regard, contemplated herein is an multimeric MR1-ligand complex of the formula $[MR1\text{-}L]_n$, when the [MR1-L] subunit is represented up to n times, in a complex with a multi-valence binding molecule having a valency of n. In an embodiment, n is for 2 to 10, including 2, 3, 4, 5, 6, 7, 8, 9 and 10.

In one example, the multi-valence binding molecule is streptavadin with a valency of 4. In this instance, $[MR1\text{-}L]_n$ is defined as being 2, 3 or 4.

In an embodiment, $[MR1\text{-}L]_n$ is labeled with a reporter molecule or means to produce a detectable signal. This is represented as $[MR1\text{-}L]_n$*.

In an embodiment, the MR1 polypeptide comprises all or part of SEQ ID NO: 1 or SEQ ID NO: 4 or a functional derivative thereof having one or more amino acid substitutions, additions and/or deletions to SEQ ID NO: 1 or SEQ ID NO: 4, for example SEQ ID NO: 2 or SEQ ID NO: 5.

In an embodiment, the MR1 polypeptide comprises at least one mutation selected from the list consisting of K43A, K43M, K43I, K43L, K43F, K43Q, Y7A, Y7W, R9K, R9A, S24F, Y62A, L66A, L66F, W69A, R94K, R94A, I96A, I96F, W156A, using single letter abbreviations for amino acid residues. The number refers to the amino acid residue number in the wild-type MR1 amino acid sequence (SEQ ID NO: 1 or SEQ ID NO: 4).

In an embodiment the MR1 comprises one or more mutations in surface exposed groups including but not limited to the list consisting of D57, R61, L65, M72, V75, R79, T138, Q141, N146, H148, L151, N155, E158, and R167. The number refers to the amino acid residue number in the mature wild-type MR1 amino acid sequence (SEQ ID NO: 1 or SEQ ID NO: 4).

In an embodiment the MR1 comprises a L43A mutation.

Enabled herein is a method of modulating MAIT cell activity, the method comprising contacting the cell with an effective amount of an MR1-ligand subunit or a multimeric complex thereof for a time and under conditions sufficient to modulate the activation of MAIT cells by facilitating activation or inhibiting MAIT cell binding.

An aspect of the present invention provides a method of down-regulating MAIT cell activity, the method comprising contacting the cell with an effective amount of [MR1-L] wherein L is 6-formyl pterin, acetyl 6-formyl pterin or a functional analog thereof or a multimeric complex comprising same for a time and under conditions sufficient to inhibit MAIT cell activation.

Another aspect of the present invention provides a method of up-regulating MAIT cell activity, the method comprising contacting the cell with an effective amount of [MR1-L] wherein L is a compound selected from the list consisting of rRL-6HM, rRL-6AM, RL-6M, RP-5PA, 6-methyl-7-hydroxy-8-ribityl lumazine, 6-,7-dimethyl-8-ribityl lumazine or functional analog's thereof including but not limited to oxidised and reduced forms thereof or a multimeric complex comprising same, for a time and under conditions sufficient to promote MAIT cell activity. In an embodiment, the cell is contacted with an effective amount of [MR1-L] wherein L is rRL-6HM or a multimeric complex comprising same.

In an embodiment the MAIT cells are human or mouse MAIT cells or MAIT cells from another mammal.

In an embodiment, the ligand or functional analog thereof is capable of binding to MR1 on an antigen presenting cell and of forming a complex with MR1 which complex modulates the activity of MAIT cells via their TCRs, herein referred to as an MR1-ligand subunit.

In an embodiment, the MR1-ligand subunit enhances the activity of the MAIT cells. In an embodiment, the MR1-ligand subunit or functional analog thereof induces the proliferation of the MAIT cells. In an embodiment, there is a complex of two or more MR1-ligand subunits.

In another embodiment, the MR1-ligand subunit inhibits the activity of the MAIT cells. In an embodiment, the MR1-ligand subunit leads to the depletion or deactivation of MAIT cells. In an embodiment, there is a complex of two or more MR1-ligand subunits.

A complex of two or more MR1-ligand subunits is referred to herein as a multimeric complex.

In an aspect, the present invention provides a method of detecting the presence of MAIT cells in a biological sample from a subject, the method comprising the steps of a) contacting the biological sample with antigen presenting cells expressing MR1 bind to a ligand or a soluble form thereof, under conditions that would allow binding of the MR1 with MAIT cells present in the sample; and b) detecting the presence of MAIT cell activity. In an embodiment, the MR1 bound to the ligand is in a multimeric complex. In an embodiment, CD69 levels are used to determine the level of MAIT cell activity.

In an embodiment, the ligand is rRL-6HM, rRL-6AM, rRL-6HM, RL-6M, RP-5PA, 6-methyl-7-hydroxy-8-ribityl lumazine, 6-,7-dimethyl-8-ribityl lumazine or functional analog's thereof including but not limited to oxidized and reduced forms thereof. In an embodiment the ligand is the compound rRL-6HM.

Another aspect contemplated herein is a method of detecting the presence of MAIT cells in a biological sample from a subject, the method comprising the steps of a) contacting the biological sample with antigen presenting cells expressing MR1 bound to a ligand or a soluble form thereof, under conditions that would allow binding of the MR1 with MAIT cells present in the sample; and b) detecting the presence of MAIT cell bound MR1 in the biological sample. In an embodiment, the MR1 bound to the ligand is in a multimeric complex.

In an embodiment, the ligand is 6-formyl pterin, acetyl 6-formyl pterin or a functional analogue thereof, or a compound selected from the list consisting of rRL-6AM, rRL-6HM, RL-6M, RP-5PA, 6-methyl-7-hydroxy-8-ribityl lumazine, 6-,7-dimethyl-8-ribityl lumazine or functional analog's thereof including but not limited to oxidised and reduced forms thereof. In an embodiment, the ligand is the compound rRL-6HM.

Taught herein is a method for the diagnosis of a condition associated with the level of activity of MAIT cells, or, more generally, to a cell mediated immune response condition involving MAIT cells.

Enabled herein is a method for the treatment and/or prophylaxis of a disease or condition in a mammal associated with cell mediated immune cells, the method comprising administering to the mammal, including a human, an amount of MR1-ligand subunit or a multimeric complex thereof for a time and under conditions effective to modulate the activity of MAIT cells, wherein promoting or otherwise agonizing the MAIT cell activity and inhibiting or otherwise antagonizing the MAIT cell activity determines the level of cell mediated immune response activity and for providing a cellular immune response modifier.

Enabled herein is a method for the treatment and/or prophylaxis of a condition characterized by excessive or insufficient MAIT cell activity in a mammal, including a human, the method comprising administering to said mammal an amount of MR1-ligand subunit or a multimeric complex thereof for a time and under conditions effective to modulate MAIT cell activation, wherein promoting or otherwise agonizing the MAIT cell activity or inhibiting or otherwise antagonizing the MAIT cell activity determines the level of cell mediated immune response activity and then providing a cellular immune response modifier.

Enabled herein is a method for the treatment and/or prophylaxis of a condition characterized by excessive MAIT cell activity in a mammal including a human, said method comprising contacting the cell with an amount of [MR1-L] wherein L is 6-formyl pterin, acetyl 6-formyl pterin or a functional analog thereof for a time and under conditions effective to inhibit MAIT cell activity.

Enabled herein is a method for the treatment and/or prophylaxis of a condition characterized by insufficient MAIT cell activity in a mammal including a human, the method comprising contacting the cell with an amount of [MR1-L] wherein L is a compound selected from the list consisting of rRL-6AM, rRL-6HM, RL-6M, RP-5PA, 6-methyl-7-hydroxy-8-ribityl lumazine, 6-,7-dimethyl-8-ribityl lumazine or functional analogs thereof including but not limited to oxidised and reduced forms thereof, for a time and under conditions effective to promote MAIT cell activity. In an embodiment, the cell is contacted with an effective amount of MR1-L wherein L is rRL-6HM.

In an embodiment, the present invention provides the use of $[MR1\text{-}L]_n$, as hereinbefore defined, in the manufacture of a medicament for the treatment of a disease or condition in a mammal, wherein the agent modulates the level of activity of MAIT cells.

In an embodiment, the present invention provides a pharmaceutical composition comprising the $[MR1\text{-}L]_n$ as herein before defined together with one or more pharmaceutically acceptable carriers and/or diluents.

In an embodiment, the present invention provides $[MR1\text{-}L]_n$ as hereinbefore defined, when used in the methods of the present invention.

Another aspect contemplated herein involves the use of combinatorial chemistry employing 6-Formyl Pterin, acetyl-6-formyl pterin or functional analogs thereof, or a compound selected from the list consisting of rRL-6HM, rRL-6AM, RL-6M, RP-5PA, 6-methyl-7-hydroxy-8-ribityl lumazine, 6-,7-dimethyl-8-ribityl lumazine or functional analogs thereof including but not limited to oxidised and reduced forms thereof used as the scaffold basis for identification of further ligands for the purpose of blocking or activating MAIT cells or generating multimer MR1-ligand reagents. In an embodiment the compound is rRL-6HM.

Another aspect contemplated herein is a method for refolding a MR1-ligand subunit or multimeric thereof complex in the presence of compounds which facilitate the ligand bound in a ring-open conformation to a residue with the MR1 amino acid sequence. In an embodiment, the compounds facilitate a Schiff base bond to an amino acid residue such as lysine (e.g. lysine 43 of human MR1 [SEQ ID NO:1], or lysine 43 of murine MR1 [SEQ ID NO: 2]. In an embodiment, the compounds are a uracil derivative such as 5-amino-6-D-ribitylamino-uracil which together with either pyruvaldehyde or glycolaldehyde form a ring-open conformation of rRL-6-$CH_2OH$ or rRL-7-OH respectively, bound to Lysine 43 of human or murine MR1 via a Schiff base bond.

In an embodiment, the present invention provides a method for detecting a ligand capable of modulating the interaction of MR1 present on antigen presenting cells with MAIT cells, the method comprising contacting antigen presenting cells expressing MR1 with a putative agent in the presence of MAIT cells and detecting an altered effect on MAIT cell activity.

In another aspect contemplated herein the ligands or functional analogs thereof, or compositions described herein can be included in kits, for example for use as diagnostic reagents for detecting the presence of MAIT cells, or for the diagnosis, treatment or prophylaxis of a disease condition associated with the level of activity of MAIT cells.

DETAILED DESCRIPTION OF THE INVENTION

Figure 1:
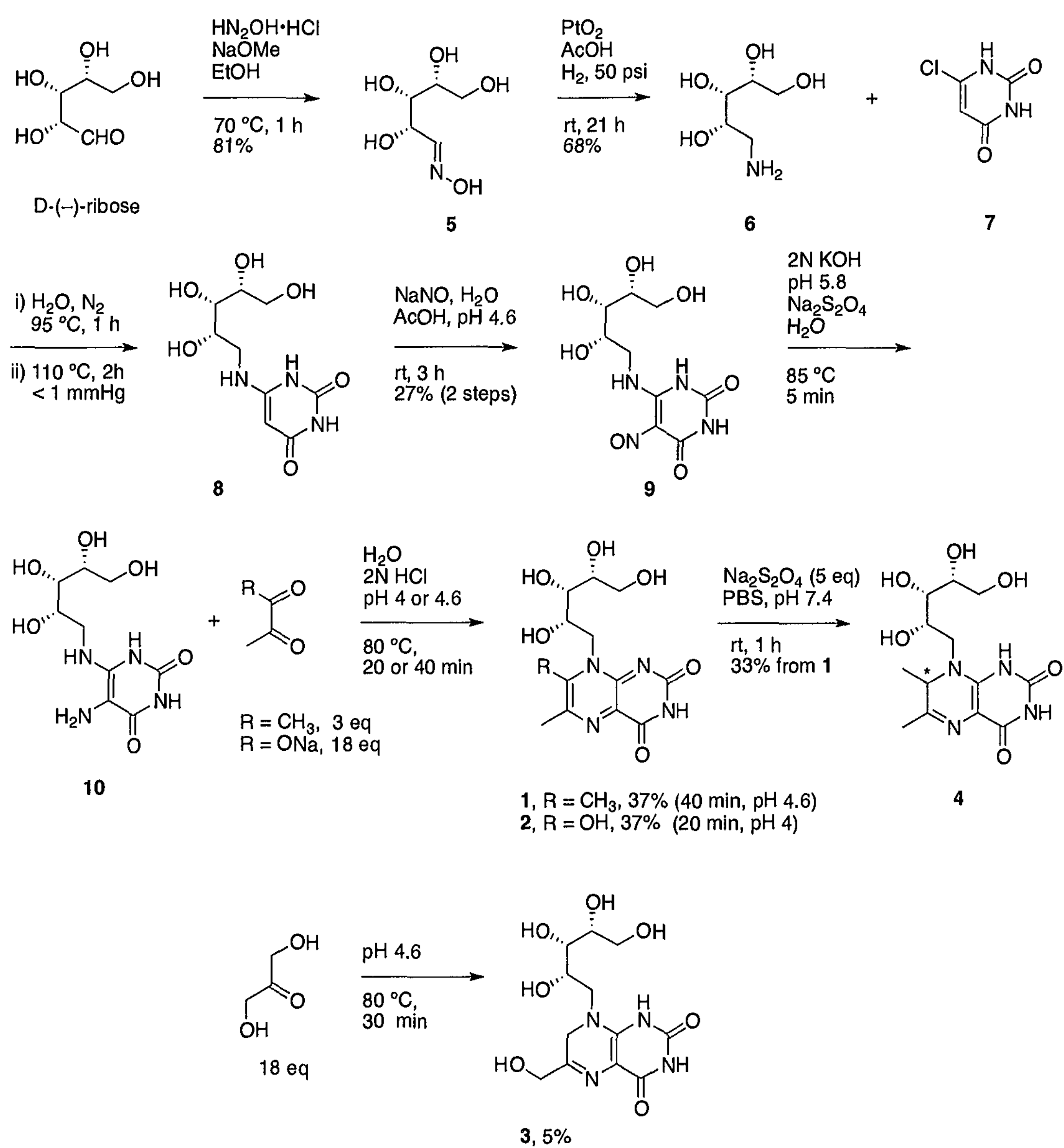
FIG. 1 is a schematic representation showing the synthetic route to the ligands of the invention.

Throughout this specification and the claims which follow, unless the context requires otherwise, the word “comprise”, and variations such as “comprises” and “comprising”, will be understood to imply the inclusion of a stated integer or step or group of integers or steps but not the exclusion of any other integer or step or group of integers or steps.

As used herein, the singular forms “a”, “an” and “the” include plural aspects unless the context clearly dictates otherwise. Thus, for example, reference to “a cell” includes a single cell, as well as two or more cells; “an agent” including a single or two or more agents; “the invention” including single or multiple aspects of an invention; and so forth.

Immunological reagents are provided that allow the preparation of MR1 bound to a ligand [MR1-L] in subunit or multimeric form $[MR1\text{-}L]_n$ that label MAIT cells according to the specificity of their antigen receptor. In an embodiment, stable multimeric complexes of MR1 subunits are provided. The multimeric MR1-ligand complexes bind the surface of MAIT cells, allowing the detection of MAIT cells. The binding complex is useful for detection, quantitation, characterization and separation of MAIT cells. Depending on the nature of the agent component of the complex in some instances the multimeric complex antagonises the activity of MAIT cells. In other instances the complex activates MAIT cells. Such activation includes, for example, enhancing their activity and/or inducing their proliferation.

In an embodiment, an MR1 subunit is provided comprising the structure $\alpha\beta$ wherein $\alpha$ is the heavy chain comprising the domains $\alpha 1$, $\alpha 2$, or $\alpha 3$ and $\beta$ is $\beta 2$-microoglobulin light chain. In an embodiment, MR1 is bound to a ligand L, i.e. [MR1-L]. In an embodiment, [MR1-L] subunit is complexed in a multimeric form $[MR1\text{-}L]_n$ wherein n is from 2 to about 10 including 2, 3, 4, 5, 6, 7, 8, 9 or 10. In an embodiment, the multimeric complex of [MR1-L] subunit is facilitated in a multi-valence binding molecule wherein the valency of the binding molecule is n and the multimeric structure comprises up to n MR1-ligand subunits.

In an embodiment, the multivalent binding molecule is streptavidin, having a valency of 4. In an embodiment, $[MR1\text{-}L]_n$ is labeled so as to produce, or has means to produce, a detection signal. Such a complex is referred to herein as $[MR1\text{-}L]_n*$.

The ability of the agents of this invention to bind to MR1 and to either inhibit or promote the activation of human MAIT cells makes them useful for numerous applications, for example, purifying mammalian and more particularly human or other primate MAIT cells via MR1-ligand tetramers, or specifically labeling mammalian and more particularly human or other primate MAIT cells in vitro, in vivo, or ex vivo. It will be appreciated that the ability to specifically purify and label MAIT cells is useful for, inter alia, diagnostic purposes as well as in application for investigating the role that MAIT cells play in immunity. This should be understood as extending to animal models other than humans or other mammalian MAIT cells.

Accordingly, in one aspect, the present invention provides a ligand or functional analogue thereof which modulates MAIT cell activity. In some embodiments, the ligand or functional analogue thereof is capable of interacting with MR1 and of forming an MR1-ligand complex which modulates the activity of MAIT Cells. Such modulating refers both to an increase or decrease in the functional immune activity of the MAIT cells.

In an embodiment the ligand is represented by formula (I):

(I)

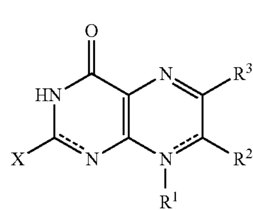

wherein:

- X is selected from the list consisting of hydroxyl, oxo, amino, mono-$C_1$-$C_3$alkylamino or di-$C_1$-$C_3$alkylamino;
- $R^1$ is present or absent and is selected from the list consisting of hydrogen, optionally substituted aryl, optionally substituted heteroaryl, and optionally substituted $C_1$-$C_{10}$alkyl;
- $R^2$ and $R^3$ are each independently selected from the list consisting of hydrogen, halogen, halo $C_1$-$C_3$alkyl, optionally substituted $C_1$-$C_3$alkoxy, optionally substituted aryl, optionally substituted heteroaryl, and optionally substituted $C_1$-$C_3$alkyl; and
- --- represents an optional double bond;

or a pharmaceutically acceptable salt, solvate, or hydrate thereof, or a tautomer or stereoisomer thereof, in any isomeric ratio, including racemates and enantiomerically enriched mixtures.

With reference to formula (I), the optional substituents include but are not limited to a group selected from may be selected from the list consisting of halogen, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4$alkyl$)_2$, —CN, —$NO_2$, mercapto, —$S(O_2)NH_2$, —$S(O_2)NHC_1$-$C_4$alkyl and $CO_2H$.

In one embodiment, the ligand interacts with MR1 and acts as an antagonist of human, rodent or other mammalian MAIT cells. In one embodiment of this aspect of the invention said ligand is 6-formyl pterin, or a functional analogue thereof. A non-limiting example of a functional analogue of 6-formyl pterin is acetyl 6-formyl pterin.

In another embodiment the ligand interacts with MR1 and activates human, rodent or other mammalian MAIT cells. In an embodiment the ligand is a compound selected from the list consisting of rRL-6HM, rRL-6AM, RL-6M, RP-5PA, 6-methyl-7-hydroxy-8-ribityl lumazine, 6-,7-dimethyl-8-ribityl lumazine, or functional analog's thereof including but not limited to oxidised and reduced forms thereof. In an embodiment said agent is the compound rRL-6HM.

It should be understood, that rRL-6HM is also known as rRL-6-$CH_2OH$ and therefore these terms are used interchangeably.

The present inventors have shown that tetramers produced from mouse MR1 are capable of staining human peripheral blood mononuclear cells (PBMCs). Accordingly, within the context of the invention, the term MR1 refers to a mammalian MR1 polypeptide. In an embodiment the MR1 polypeptide is human, primate or mouse MR1 polypeptide. In an embodiment the MR1 is from a mouse or a human.

In an embodiment the MR1 polypeptide of this invention comprises all or part of SEQ ID NO: 1 (identified in Genbank as ID NO U22963) for example, SEQ ID NO: 2 or a functional derivative thereof, having one or more amino acid substitutions, additions and/or deletions to SEQ ID NO:1 or SEQ ID NO: 2.

```
SEQ ID NO: 1: (This is fully translated human MR1,
including Leader Sequence.)
MGELMAFLLPLIIVLMVKHSDSRTHSLRYFRLGVSDPIHGVPEFISVGYV
DSHPITTYDSVTRQKEPRAPWMAENLAPDHWERYTQLLRGWQQMFKVELK
RLQRHYNHSGSHTYQRMIGCELLEDGSTTGFLQYAYDGQDFLIFNKDTLS
WLAVDNVAHTIKQAWEANQHELLYQKNWLEEECIAWLKRFLEYGKDTLQR
TEPPLVRVNRKETFPGVTALFCKAHGFYPPEIYMTWMKNGEEIVQEIDYG
DILPSGDGTYQAWASIELDPQSSNLYSCHVEHCGVHMVLQVPQESETIPL
VMKAVSGSIVLVIVLAGVGVLVWRRRPREQNGAIYLPTPDR.

SEQ ID NO: 2: (This is mature human MR1, without
Leader sequence)
RTHSLRYFRLGVSDPIHGVPEFISVGYVDSHPITTYDSVTRQKEPRAPWM
AENLAPDHWERYTQLLRGWQQMFKVELKRLQRHYNHSGSHTYQRMIGCEL
LEDGSTTGFLQYAYDGQDFLIFNKDTLSWLAVDNVAHTIKQAWEANQHEL
LYQKNWLEEECIAWLKRFLEYGKDTLQRTEPPLVRVNRKETFPGVTALFC
KAHGFYPPEIYMTWMKNGEEIVQEIDYGDILPSGDGTYQAWASIELDPQS
SNLYSCHVEHCGVHMVLQVPQESETIPLVMKAVSGSIVLVIVLAGVGVLV
WRRRPREQNGAIYLPTPDR.

SEQ ID NO: 3: Human Leader sequence:
MGELMAFLLPLIIVLMVKHSDS
```

In an embodiment the MR1 polypeptide of this invention comprises all or part of SEQ ID NO: 4 (identified in Genbank as at NM008209) for example, SEQ ID NO: 5 or a functional derivative thereof, having one or more amino acid substitutions, additions and/or deletions to SEQ ID NO: 4 or SEQ ID NO: 5.

```
SEQ ID NO: 4: (This is fully translated murine
MR1, including Leader sequence)
MMLLLPLLAVFLVKRSHTRTHSLRYFRLAVSDPGPVVPEFISVGYVDSHP
ITTYDSVTRQKEPKAPWMAENLAPDHWERYTQLLRGWQQTFKAELRHLQR
HYNHSGLHTYQRMIGCELLEDGSTTGFLQYAYDGQDFIIFNKDTLSWLAM
DYVAHITKQAWEANLHELQYQKNWLEEECIAWLKRFLEYGRDTLERTEHP
```

-continued

```
VVRTTRKETFPGITTFFCRAHGFYPPEISMTWMKNGEEIAQEVDYGGVLP
SGDGTYQTWLSVNLDPQSNDVYSCHVEHCGRQMVLEAPRESGDILRVSTI
SGTTILIIALAGVGVLIWRRSQELKEVMYQPTQVNEGSSPS
```

```
SEQ ID NO: 5: (This is mature murine MR1 lacking
Leader sequence)
RTHSLRYFRLAVSDPGPVVPEFISVGYVDSHPITTYDSVTRQKEPKAPWM
AENLAPDHWERYTQLLRGWQQTFKAELRHLQRHYNHSGLHTYQRMIGCEL
LEDGSTTGFLQYAYDGQDFIIFNKDTLSWLAMDYVAHITKQAWEANLHEL
QYQKNWLEEECIAWLKRFLEYGRDTLERTEHPVVRTTRKETFPGITTFFC
RAHGFYPPEISMTWMKNGEEIAQEVDYGGVLPSGDGTYQTWLSVNLDPQS
NDVYSCHVEHCGRQMVLEAPRESGDILRVTISGTTILIIALAGVGVLIWR
RSQELKEVMYQPTQVNEGSSPS
```

```
SEQ ID NO: 6: Mouse Leader sequence:
MMLLLPLLAVFLVKRSHT
```

SEQ ID NOs: 2 and 5 represent the human and mouse mature MR1 protein sequences, respectively, with the translated leader sequence removed. SEQ ID NOs: 1 and 4 represent the human and mouse MR1 protein sequences, respectively, including the translated leader sequence. The translated leader sequence for the human and mouse MR1 protein sequences are represented by SEQ ID NOs: 3 and 6, respectively. Table 1 provides a summary of the MR1 sequences.

TABLE 1

| SEQ ID NO | MR1 Sequence |
|---|---|
| 2 | Mature MR1 protein - human |
| 1 | Mature MR1 protein + leader sequence - human |
| 3 | MR1 leader sequence - human |
| 5 | Mature MR1 protein - mouse |
| 4 | Mature MR1 protein + leader sequence - mouse |
| 6 | MR1 leader sequence - mouse |

Reference to parts thereof means any portion of which contains functional domains, such as the ligand binding site. Functional derivatives include naturally-occurring variants, for example, polymorphisms, splicing forms, homologs from other species, etc. It also includes synthetic derivatives, i.e., artificially created MR1 polypeptides having modified amino acid sequence as compared to SEQ ID NO: 1 (U22963) or SEQ ID NO: 2 (NM008209). Modification of amino acid sequence includes any mutation, deletion, or addition thereof including modifications introduced for the purpose of creating multimeric forms of the MR1-ligand subunit for diagnostic, research or therapeutic applications. Functional derivative means that MR1 polypeptide retains the ability to bind MAIT cells or a specific receptor thereof or to bind a ligand of MR1.

In an embodiment, the introduction of certain mutations in the MR1 sequence enables the production of MR1 compound tetramers with enhanced MAIT cell binding ability. Accordingly, in one embodiment, the MR1 utilized in accordance with the invention comprises at least one mutation selected from the list consisting of K43A, K43M, K43I, K43L, K43F, K43Q, Y7A, Y7W, R9K, R9A, S24F, Y62A, L66A, L66F, W69A, R94K, R94A, I96A, I96F, W156A. Also contemplated are mutations in surface exposed groups including but not limited to the list consisting of D57, R61, L65, M72, V75, R79, T138, Q141, N146, H148, L151, N155, E158, and R167. The number refers to the amino acid residue number in the wild-type mature amino acid sequences (SEQ ID NO: 1 and SEQ ID NO: 2).

In an embodiment the MR1 comprises a L43A mutation.

In forming the MR1-ligand complexes, the MR1 subunits are expressed in a suitable host cell, and, if necessary, solubilized. The subunits are combined with an antigenic compound and allowed to fold in vitro to form a stable heterodimer complex with intrachain disulfide bonded domains. The compound may be included in the initial folding reaction, or may be added to the empty heterodimer in a later step. Usually the MR1 binding site will be free prior to addition of the target antigenic compound. The exception will be those cases where it is desirable to label the MAIT cells with a natural ligand-MHC complex, such as those that may be present on the surface of cells that are a target for autoimmune attack, etc.

In an embodiment, MR1 will bind an antigenic compound in the groove formed by the two membrane distal domains, either $\alpha 2$ and $\alpha 1$.

Conditions that permit folding and association of MR1 and ligands are known in the art, see for example Altman et al. (1993) and Garboczi et al. (1992). It will be readily understood by one of skill in the art that the specific folding conditions are not critical for the practice of the invention.

The ligands may be prepared in a variety of ways. Conveniently, they can be synthesized by conventional techniques employing automatic synthesizers, or may be synthesized manually. The ligands may also be isolated from natural sources and purified by known techniques, including, for example, chromatography on ion exchange materials, separation by size, immunoaffinity chromatography and electrophoresis.

The monomeric MR1-ligand complex has the formula ([MR1]-L) (herein MR1-ligand subunit). [MR1] comprises a heavy chain comprising domains $\alpha 1$, $\alpha 2$ or $\alpha 3$ of MR1 and a $\beta 2$ microglobulin chain. L is a ligand including an antigen or chemically derived binding agent.

The multimeric complexes described herein have enhanced ability to bind MAIT cells or enhanced ability to inhibit MAIT cell activation. Accordingly, in an embodiment the MR1-ligand subunits are multimeric including dimers, trimers and tetramers of MR1 or of TCR (V$\alpha$7.2-J$\alpha$33/V$\beta$13) complexed with the agent as well as multimeric forms up to about 10 subunits.

The multimeric binding complex has the formula $[MR1\text{-}L]_n$, where $n \geq 2$, usually $n \geq 4$, and usually $n \leq 10$. The multimeric complex stably binds through non-covalent interactions to a MAIT cell receptor having the appropriate antigenic specificity. When compared to the binding of an [MR1-L] "monomer" subunit to a MAIT cell, the binding complex will have greatly increased stability, usually having an increase of at least about 10-fold in t½, more usually an increase of about 20-fold, and may be increased as much as about 50-fold.

The resulting multimer will be stable over long periods of time. Usually not more than about 10% of the multimer will be dissociated after storage at 4. In an embodiment, the multimer will be formed by binding the monomers to a multivalent entity through specific attachment sites on the $\alpha$ or $\beta$ subunit, as described below in detail. The multimer may also be formed by chemical cross-linking of the monomers. A number of reagents capable of cross-linking proteins are known in the art, illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl] aminobenzoate, glutaraldehyde, formaldehyde and succinimidyl 4-[N-maleimidomethyl]cyclohexane-1-carboxylate.

The attachment site for binding to a multivalent entity may be naturally occurring, or may be introduced through genetic engineering. The site will be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain. In a preferred embodiment, one of the subunits is fused to an amino acid sequence providing a recognition site for a modifying enzyme. The recognition sequence will usually be fused proximal to the carboxy terminus of one of the subunit to avoid potential hindrance at the antigenic agent binding site.

Modifying enzymes of interest include BirA, various glycosylases, farnesyl protein transferase, protein kinases and the like. The subunit may be reacted with the modifying enzyme at any convenient time, usually after formation of the monomer. The group introduced by the modifying enzyme, e.g. biotin, sugar, phosphate, farnesyl, etc. provides a complementary binding pair member, or a unique site for further modification, such as chemical cross-linking, biotinylation, etc. that will provide a complementary binding pair member. An alternative strategy is to introduce an unpaired cysteine residue to the subunit, thereby introducing a unique and chemically reactive site for binding. The attachment site may also be a naturally occurring or introduced epitope, where the multivalent binding partner will be an antibody, e.g. IgG, IgM, etc. Any modification will be at a site, e.g. C-terminal proximal, that will not interfere with binding.

Exemplary of multimer formation is the introduction of the recognition sequence for the enzyme BirA, which catalyzes biotinylation of the protein substrate. The monomer with a biotinylated subunit is then bound to a multivalent binding partner, e.g. streptavidin or avidin, to which biotin binds with extremely high affinity. Streptavidin has a valency of 4, providing a multimer of $[MR1\text{-}L]_4$.

The multivalent binding partner may be free in solution, or may be attached to an insoluble support. Examples of suitable insoluble supports include beads, e.g. magnetic beads, membranes and microtiter plates. These are typically made of glass, plastic (e.g. polystyrene), polysaccharides, nylon or nitrocellulose. Attachment to an insoluble support is useful when the binding complex is to be used for separation of MAIT cells.

Frequently, the multimeric complex will be labeled, so as to be directly detectable, or will be used in conjunction with secondary labeled immunoreagents which will specifically bind the complex. In general the label will have a light detectable characteristic. Preferred labels are fluorophors, such as fluorescein isothiocyanate (FITC), rhodamine, Texas Red, phycoerythrin and allophycocyanin. Other labels of interest may include dyes, enzymes, chemiluminescers, particles, radioisotopes, or other directly or indirectly detectable agent. Conveniently, the multivalent binding partner will have the labeling group. Alternatively, a second stage label may be used.

The binding complex will be used to detect and/or separate antigen bound MAIT cells. The MAIT cells may be from any source, usually having the same species of origin as the MR1 heterodimer.

As used herein, the term "MAIT" cells, or "Mucosal-Associated Invariant T cells" refers to a population of T cells present in mammals, preferably humans, that generally display an invariant TCR alpha chain comprising Vα7.2-Jα33 (in humans), a CDR3 of constant length, and a limited number of Vβ segments together with an activated phenotype (CD44) (see, for example, Lantz and Bendelac. (1994); Tilloy et al. (1999); Treiner et al. (2003), the entire disclosures of each of which are herein incorporated by reference). This includes MAIT cells defined as MR1-Ag tetramer-positive by flow or other tagging methods not expressing canonical Vα7.2-Jα33 TCR but functionally MAIT cells in their Ag-specificity. In an embodiment, MAIT cells are generally $CD4^+$ or $CD4^-/CD8^-$ (DN) or CD8αα in humans, and are restricted by the non-classical MHC class I molecule MR1. In an embodiment, MAIT cells can be defined as $CD3^+$ $CD4^-$ $CD161^+$ $TRAV1.2^+$ (monoclonal antibody $D5^+$). In terms of localization, MAIT cells are considered to be generally absent from the thymus, liver, spleen and bone marrow, but are abundant in the gut lamina-propria (LP), the mesenteric lymph nodes (MLN), and in other mucosal tissues, such as the lungs. For the purposes of the present invention, in an embodiment, T cells that express the invariant Vα7.2-Jα33 alpha TCR chain are considered to be predominantly MAIT cells including the possibility that some T cells that do not express the invariant Vα7.2-Jα33 alpha TCR chain may also recognize MAIT ligands and function as MAIT cells. Mostly, the invariant alpha chain is associated with an invariant CDR3 and with either Vβ2 or Vβ13. Also in an embodiment, the MAIT cells are present in a mucosal tissue, such as the gut or more specifically but not limited to, the gut lamina propria the mesenteric lymph nodes, the mucosal surfaces of the oral cavity, conjunctiva, reproductive tract, bladder and urinary tract, foreskin, the lungs, the esophagus, stomach, small intestine (as above), large intestine, rectum and peri-anal tissue.

In an embodiment, the MAIT cells are mouse or human cells or cells from other mammals.

The MAIT cells may be from an in vitro culture, or a physiologic sample. For the most part, the physiologic samples employed will be blood or lymph, but samples may also involve other sources oft cells, particularly where MAIT cells may be invasive. Thus other sites of interest are tissues, or associated fluids, as in the brain, lymph node, neoplasms, spleen, liver, kidney, pancreas, tonsil, thymus, joints, synovia, and the like. The sample may be used as obtained or may be subject to modification, as in the case of dilution, concentration, or the like. Prior treatments may involve removal of cells by various techniques, including centrifugation, using Ficoll-Hypaque, panning, affinity separation, using antibodies specific for one or more markers present as surface membrane proteins on the surface of cells, or any other technique that provides enrichment of the set or subset of cells of interest.

In an embodiment, the MR1-ligand subunit or multimeric complex thereof is added to a suspension comprising MAIT cells of interest, and incubated at about 4 degrees sufficient to bind the available cell surface receptor. The incubation will usually be at least about 5 minutes and usually less than about 30 minutes. It is desirable to have a sufficient concentration of labeling reagent in the reaction mixture, so that labeling reaction is not limited by lack of labeling reagent. The appropriate concentration is determined by titration. The medium in which the cells are labeled will be any suitable medium as known in the art. If live cells are desired a medium will be chosen that maintains the viability of the cells. In an embodiment the medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

Where a second stage labeling reagent is used, the cell suspension may be washed and resuspended in medium as described above prior to incubation with the second stage reagent. Alternatively, the second stage reagent may be added directly into the reaction mix.

A number of methods for detection and quantitation of labeled cells are known in the art. Flow cytometry is a convenient means of enumerating cells that are a small percent of the total population. Fluorescent microscopy may also be used. Various immunoassays, e.g. ELISA, RIA, etc. may used to quantitate the number of cells present after binding to an insoluble support.

Flow cyometry may also be used for the separation of a labeled subset of MAIT cells from a complex mixture of cells. The cells may be collected in any appropriate medium which maintains the viability of the cells, usually having a cushion of serum at the bottom of the collection tube. Various media are commercially available as described above. The cells may then be used as appropriate.

Alternative means of separation utilize the MR1-ligand subunit or multimeric complex thereof bound directly or indirectly to an insoluble support, e.g. column, microtiter plate, magnetic beads, etc. The cell sample is added to the binding complex. The MR1-ligand subunit or multimeric complex thereof may be bound to the support by any convenient means. After incubation, the insoluble support is washed to remove non-bound components. From one to six washes may be employed, with sufficient volume to thoroughly wash non-specifically bound cells present in the sample. The desired cells are then eluted from the MR1-ligand subunit or multimeric complex thereof. In particular the use of magnetic particles to separate cell subsets from complex mixtures is described in Miltenyi et al. (1990) Cytometry 11:231-238.

Detecting and/or quantitating MAIT cells in a sample or fraction thereof may be accomplished by a variety of specific assays which will known in the art, such as, for example, sandwich or ELISA assays. In general, the assay will measure the binding between a patient sample, usually blood derived, generally in the form of plasma or serum and the subject multimeric binding complexes. The patient sample may be used directly, or diluted as appropriate, usually about 1:10 and usually not more than about 1:10,000. Assays may be performed in any physiological buffer, e.g. PBS, normal saline, HBSS, dPBS, etc.

The MR1-subunit or multimeric complex thereof as herein described of the invention may be provided in non-soluble or soluble form, depending on the intended application.

In one embodiment the MR1-ligand subunit or multimeric complex thereof is between 50,000 Da and 1,000,000 Da, such as from 50,000 Da to 980,000; for example from 50,000 Da to 960,000; such as from 50,000 Da to 940,000; for example from 50,000 Da to 920,000; such as from 50,000 Da to 900,000; for example from 50,000 Da to 880,000; such as from 50,000 Da to 860,000; for example from 50,000 Da to 840,000; such as from 50,000 Da to 820,000; for example from 50,000 Da to 800,000; such as from 50,000 Da to 780,000; for example from 50,000 Da to 760,000; such as from 50,000 Da to 740,000; for example from 50,000 Da to 720,000; such as from 50,000 Da to 700,000; for example from 50,000 Da to 680,000; such as from 50,000 Da to 660,000; for example from 50,000 Da to 640,000; such as from 50,000 Da to 620,000; for example from 50,000 Da to 600,000; such as from 50,000 Da to 580,000; for example from 50,000 Da to 560,000; such as from 50,000 Da to 540,000; for example from 50,000 Da to 520,000; such as from 50,000 Da to 500,000; for example from 50,000 Da to 480,000; such as from 50,000 Da to 460,000; for example from 50,000 Da to 440,000; such as from 50,000 Da to 420,000; for example from 50,000 Da to 400,000; such as from 50,000 Da to 380,000; for example from 50,000 Da to 360,000; such as from 50,000 Da to 340,000; for example from 50,000 Da to 320,000; such as from 50,000 Da to 300,000; for example from 50,000 Da to 280,000; such as from 50,000 Da to 260,000; for example from 50,000 Da to 240,000; such as from 50,000 Da to 220,000; for example from 50,000 Da to 200,000; such as from 50,000 Da to 180,000; for example from 50,000 Da to 160,000; such as from 50,000 Da to 140,000; for example from 50,000 Da to 120,000; such as from 50,000 Da to 100,000; for example from 50,000 Da to 80,000; such as from 50,000 Da to 60,000; such as from 100,000 Da to 980,000; for example from 100,000 Da to 960,000; such as from 100,000 Da to 940,000; for example from 100,000 Da to 920,000; such as from 100,000 Da to 900,000; for example from 100,000 Da to 880,000; such as from 100,000 Da to 860,000; for example from 100,000 Da to 840,000; such as from 100,000 Da to 820,000; for example from 100,000 Da to 800,000; such as from 100,000 Da to 780,000; for example from 100,000 Da to 760,000; such as from 100,000 Da to 740,000; for example from 100,000 Da to 720,000; such as from 100,000 Da to 700,000; for example from 100,000 Da to 680,000; such as from 100,000 Da to 660,000; for example from 100,000 Da to 640,000; such as from 100,000 Da to 620,000; for example from 100,000 Da to 600,000; such as from 100,000 Da to 580,000; for example from 100,000 Da to 560,000; such as from 100,000 Da to 540,000; for example from 100,000 Da to 520,000; such as from 100,000 Da to 500,000; for example from 100,000 Da to 480,000; such as from 100,000 Da to 460,000; for example from 100,000 Da to 440,000; such as from 100,000 Da to 420,000; for example from 100,000 Da to 400,000; such as from 100,000 Da to 380,000; for example from 100,000 Da to 360,000; such as from 100,000 Da to 340,000; for example from 100,000 Da to 320,000; such as from 100,000 Da to 300,000; for example from 100,000 Da to 280,000; such as from 100,000 Da to 260,000; for example from 100,000 Da to 240,000; such as from 100,000 Da to 220,000; for example from 100,000 Da to 200,000; such as from 100,000 Da to 180,000; for example from 100,000 Da to 160,000; such as from 100,000 Da to 140,000; for example from 100,000 Da to 120,000; such as from 150,000 Da to 980,000; for example from 150,000 Da to 960,000; such as from 150,000 Da to 940,000; for example from 150,000 Da to 920,000; such as from 150,000 Da to 900,000; for example from 150,000 Da to 880,000; such as from 150,000 Da to 860,000; for example from 150,000 Da to 840,000; such as from 150,000 Da to 820,000; for example from 150,000 Da to 800,000; such as from 150,000 Da to 780,000; for example from 150,000 Da to 760,000; such as from 150,000 Da to 740,000; for example from 150,000 Da to 720,000; such as from 150,000 Da to 700,000; for example from 150,000 Da to 680,000; such as from 150,000 Da to 660,000; for example from 150,000 Da to 640,000; such as from 150,000 Da to 620,000; for example from 150,000 Da to 600,000; such as from 150,000 Da to 580,000; for example from 150,000 Da to 560,000; such as from 150,000 Da to 540,000; for example from 150,000 Da to 520,000; such as from 150,000 Da to 500,000; for example from 150,000 Da to 480,000; such as from 150,000 Da to 460,000; for example from 150,000 Da to 440,000;

such as from 150,000 Da to 420,000; for example from 150,000 Da to 400,000; such as from 150,000 Da to 380,000; for example from 150,000 Da to 360,000; such as from 150,000 Da to 340,000; for example from 150,000 Da to 320,000; such as from 150,000 Da to 300,000; for example from 150,000 Da to 280,000; such as from 150,000 Da to 260,000; for example from 150,000 Da to 240,000; such as from 150,000 Da to 220,000; for example from 150,000 Da to 200,000; such as from 150,000 Da to 180,000; for example from 150,000 Da to 160,000.

In another preferred embodiment the MR1-ligand subunit or multimeric complex thereof is between 1,000,000 Da and 3,000,000 Da, such as from 1,000,000 Da to 2,800,000; for example from 1,000,000 Da to 2,600,000; such as from 1,000,000 Da to 2,400,000; for example from 1,000,000 Da to 2,200,000; such as from 1,000,000 Da to 2,000,000; for example from 1,000,000 Da to 1,800,000; such as from 1,000,000 Da to 1,600,000; for example from 1,000,000 Da to 1,400,000.

In an embodiment, 6-formyl pterin and acetyl 6-formyl pterin can form a covalent bond between the 6-FP formyl group and Lysine 43 of the MR1 heavy chain, thereby stabilizing the MR1-ligand interaction and enhancing the function of these ligands. Accordingly, in an embodiment modification of MR1 by a ligand as described herein has the effect of stabilizing the MR1-ligand complex and extending its half-life. As the skilled person would appreciate this has significant application for analytical or therapeutic purposes.

In one embodiment, the MR1-ligand subunit or multimeric complex thereof enhances the activity of the MAIT cells. In another embodiment, the MR1-ligand subunit or multimeric complex thereof induces the proliferation of the MAIT cells. In an embodiment, the MR1-ligand subunit or multimeric complex thereof induces the production by MAIT cells of TNF, Interferon gamma, RANTES, IL-10, IL-17 and/or other key cytokines or chemokines that regulate immunity or the expression of CD69 on MAIT cells.

In an embodiment the ligand is represented by formula (I):

(I)

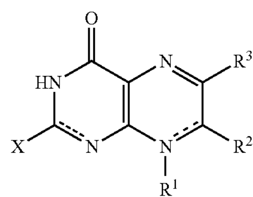

wherein:

X is selected from the list consisting of hydroxyl, oxo, amino, mono-$C_1$-$C_3$alkylamino or di-$C_1$-$C_3$alkylamino;

$R^1$ is present or absent and is selected from the list consisting of hydrogen, optionally substituted aryl, optionally substituted heteroaryl, and optionally substituted $C_1$-$C_{10}$alkyl;

$R^2$ and $R^3$ are each independently selected from the list consisting of hydrogen, halogen, halo $C_1$-$C_3$alkyl, optionally substituted $C_1$-$C_3$alkoxy, optionally substituted aryl, optionally substituted heteroaryl, and optionally substituted $C_1$-$C_3$alkyl; and --- represents an optional double bond;

or a pharmaceutically acceptable salt, solvate, or hydrate thereof, or a tautomer or stereoisomer thereof, in any isomeric ratio, including racemates and enantiomerically enriched mixtures.

With reference to formula (I), the optional substituents include but are not limited to a group selected from the list consisting of halogen, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4alkyl)_2$, —CN, —$NO_2$, mercapto, —$S(O_2)NH_2$, —$S(O_2)NHC_1$-$C_4$alkyl and $CO_2H$.

In an embodiment the ligand is rRL-6AM, rRL-6HM, RL-6M, RP-5PA, 6-methyl-7-hydroxy-8-ribityl lumazine, 6-,7-dimethyl-8-Ribityl Lumazine or functional analogues thereof including oxidised and reduced forms thereof. In a preferred embodiment said agent is the compound rRL-6HM. In an embodiment the ligand is the compound rRL-6-$CH_2$OH.

In another embodiment, the MR1-ligand subunit or multimeric complex thereof inhibits the activity of the MAIT cells. In one embodiment, MR1-ligand subunit or multimeric complex thereof leads to the depletion or apoptosis of MAIT cells. For example, the MR1-ligand subunit or multimeric complex thereof can also readily be modified so as to have properties of decreasing MAIT cell function, for example, by causing their depletion, for example, by including a toxic moiety, or driving antigen-induced MAIT cell apoptosis or by mediating depletion of the antibody-bound MAIT by cellular effectors.

In an embodiment the ligand is represented by formula (I):

(I)

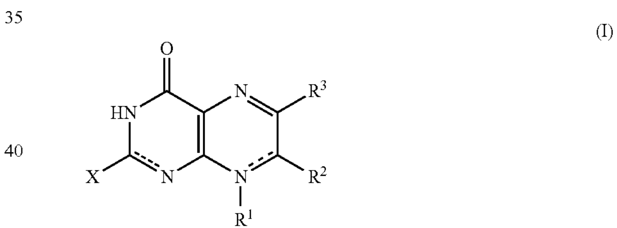

wherein:

X is selected from the list consisting of hydroxyl, oxo, amino, mono-$C_1$-$C_3$alkylamino or di-$C_1$-$C_3$alkylamino;

$R^1$ is present or absent and is selected from the list consisting of hydrogen, optionally substituted aryl, optionally substituted heteroaryl, and optionally substituted $C_1$-$C_{10}$alkyl;

$R^2$ and $R^3$ are each independently selected from the list consisting of hydrogen, halogen, halo $C_1$-$C_3$alkyl, optionally substituted $C_1$-$C_3$alkoxy, optionally substituted aryl, optionally substituted heteroaryl, and optionally substituted $C_1$-$C_3$alkyl; and --- represents an optional double bond;

or a pharmaceutically acceptable salt, solvate, or hydrate thereof, or a tautomer or stereoisomer thereof, in any isomeric ratio, including racemates and enantiomerically enriched mixtures.

With reference to formula (I), the optional substituents include but are not limited to a group selected from the list consisting of halogen, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-

$C_4$alkyl, —N($C_1$-$C_4$alkyl)$_2$, —CN, —$NO_2$, mercapto, —S($O_2$)$NH_2$, —S($O_2$)NH$C_1$-$C_4$alkyl and $CO_2$H.

In an embodiment the ligand is a compound selected from the list consisting of rRL-6HM, RL-6M, RP-5PA, 6-formyl pterin, acetyl-6-formyl pterin or related analogues or the agent 6-methyl-7-hydroxy-8-ribityl lumazine, 6-,7-dimethyl-8-Ribityl Lumazine or functional analogues thereof including oxidised and reduced forms thereof. In an embodiment the ligand is the compound rRL-6HM.

The activity of MAIT cells of this invention can be assessed by standard methods known in the art for assessing cellular activity. In a non-limiting example, the activity of MAIT cells of this invention is assessed in a assay in which MAIT cells are incubated in the presence or absence of the agent of the invention and with antigen presenting cells such as for example, B cells presenting the MHC class Ib molecule, MR1. Optionally, microbial flora is also present in the incubation. The effect of the presence of the agent on the properties of the B or T cells, for example, their proliferation, activity, cytotoxicity, Ig production, or production of cytokines such as IL-10, RANTES, TNF-β, TNF-α or IFN-γ are assessed. In other examples, assays may examine MAIT cell surface activation markers such as CD69, IL2R by flow cytometric techniques; alternatively, cytokine production of MAIT cells in response to ligand stimulation or blockade might evaluate a broad array of cytokines production by flow-based, cytokine array methods. In another illustrative example, the activity of MAIT cells can be assessed by ELISPOT assays which might enumerate MAIT cells through their individual cytokine production or other surrogate marred of cellular activation in response to ligand stimulation or blockade. In a non limiting example, MAIT cell activation can be assayed by CD69 upregulation and intracellular cytokine staining for interferon (IFN-γ) and tumor necrosis factor (TNF).

In one embodiment, the MR1-ligand subunit or multimeric complex thereof causes an increase or decrease in MAIT cell activity of at least about 10%, 20%, 30%, 40%, 50%, or more, or alternatively, causes an increase or decrease in MAIT cell proliferation by at least about 10%, 20%, 30%, 40%, 50%, or more.

The terms "decrease", "inhibit" and "down-regulate" with respect to MAIT cells means the slowing down, reducing, or reversing, or in any way negatively affecting the activity of MAIT cells, preferably functional immune activity and/or number of MAIT cell receptors including but by no means limited to MAIT cells expressing Vα7.2-Jα33. The terms "increase", "enhance" and "up-regulate" with respect to MAIT cells means the increasing, enhancing or in any way positively affecting the activity of MAIT cells, preferably functional immune activity and/or number of MAIT cell receptors including but by no means limited to MAIT cells expressing Vα7.2-Jα33.

It will be appreciated that, Vα7.2-Jα33 is a common T cell receptor expressed by MAIT cells. As used herein, "Vα7.2-Jα33" includes any variant, derivative, or isoform of the rearranged Vα7.2-Jα33 gene or encoded protein.

The determination of the ligands which bind MR1 and either inhibit or promote the activation of human MAIT cells enables the design of methods for detecting the presence of MAIT cells.

Accordingly, in another aspect, the present invention provides a method of detecting the presence of MAIT cells in a biological sample form a subject, the method comprising the steps of a) contacting the biological sample with antigen presenting cells expressing MR1 bind to a ligand or a soluble form thereof, under conditions that would allow binding of the MR1, with MAIT cells present in the sample; and b) detecting the presence of MAIT cell activity. In an embodiment, the MR1 bound to the ligand is in a multimeric complex. In an embodiment, CD69 levels are used to determine the level of MAIT cell activity.

In another aspect, the present invention provides a method of detecting the presence of MAIT cells in a biological sample from a subject, the method comprising the steps of a) contacting the biological sample with antigen presenting cells expressing MR1 bound to a ligand or a soluble form thereof, under conditions that would allow binding of the MR1 with MAIT cells present in the sample; and b) detecting the presence of MAIT cell bound MR1 in the biological sample. In an embodiment, the MR1 bound to the ligand is in a multimeric complex.

In one embodiment, the MR1 bound to a ligand or a soluble form thereof is conjugated or covalently bound to a detectable moiety.

In an embodiment the ligand is represented by formula (I):

(I)

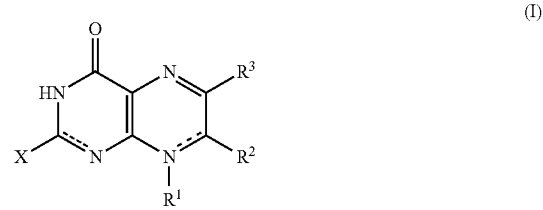

wherein:

X is selected from the list consisting of hydroxyl, oxo, amino, mono-$C_1$-$C_3$alkylamino or di-$C_1$-$C_3$alkylamino;

$R^1$ is present or absent and is selected from the list consisting of hydrogen, optionally substituted aryl, optionally substituted heteroaryl, and optionally substituted $C_1$-$C_{10}$alkyl;

$R^2$ and $R^3$ are each independently selected from the list consisting of hydrogen, halogen, halo $C_1$-$C_3$alkyl, optionally substituted $C_1$-$C_3$alkoxy, optionally substituted aryl, optionally substituted heteroaryl, and optionally substituted $C_1$-$C_3$alkyl; and --- represents an optional double bond;

or a pharmaceutically acceptable salt, solvate, or hydrate thereof, or a tautomer or stereoisomer thereof, in any isomeric ratio, including racemates and enantiomerically enriched mixtures.

With reference to formula (I), the optional substituents include but are not limited to a group selected from the list consisting of halogen, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —NH$C_1$-$C_4$alkyl, —N($C_1$-$C_4$alkyl)$_2$, —CN, —$NO_2$, mercapto, —S($O_2$)$NH_2$, —S($O_2$)NH$C_1$-$C_4$alkyl and $CO_2$H.

In a further embodiment the ligand is represented by formula (Ia); or salts, solvates, tautomers, stereoisomers, or oxidised forms thereof:

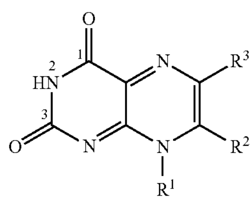

wherein:

$R^1$ is a $C_1$-$C_6$alkyl group substituted 1 to 6 times with hydroxyl;

$R^2$ is selected from the list consisting of hydrogen, hydroxyl, $C_1$-$C_3$alkyl or $C_1$-$C_3$alkoxy, and $R^3$ is selected from the list consisting of hydrogen, $C_1$-$C_3$alkyl, $C_1$-$C_3$alkoxy, —$C_1$-$C_3$alkylene-hydroxyl, or —$C_1$-$C_3$alkylene-amino.

In an embodiment $R^1$ is

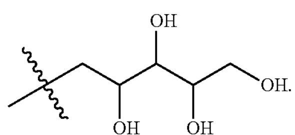 [SMILES: *CC(O)C(O)C(O)CO]

In an embodiment $R^1$ is derived from ribose, arabinose, xylose or lyxose.

In an embodiment $R^1$ is derived from D-ribose, D-arabinose, D-xylose, or D-lyxose.

In an embodiment $R^2$ is hydrogen, $CH_3$, $OCH_3$ or OH.

In an embodiment $R^2$ is hydrogen.

In an embodiment $R^3$ is —$CH_2OH$, —$CH_2CH_2OH$, —$CH_2NH_2$, —$CH_2CH_2NH_2$, —$CH_3$, or —$CH_2CH_3$.

In an embodiment $R^3$ is —$CH_2OH$ or —$CH_2NH_2$.

In an embodiment $R^3$ is —$CH_2OH$.

In an embodiment $R^3$ is —$CH_2NH_2$.

In an embodiment the compound of formula (Ia) is represented by one of the following formulae:

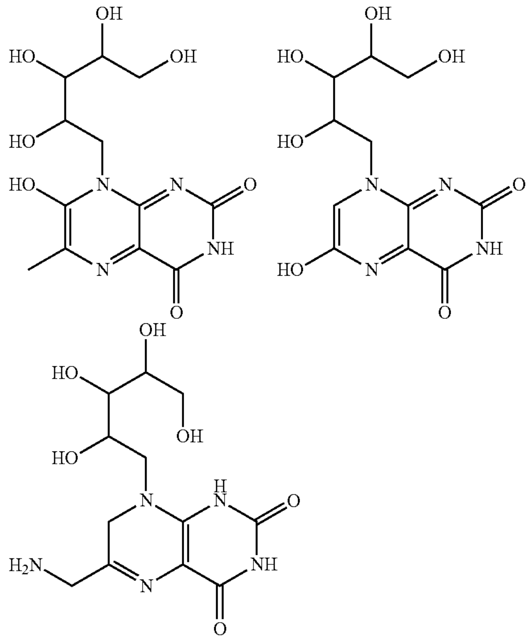

-continued

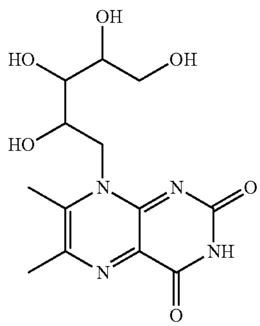

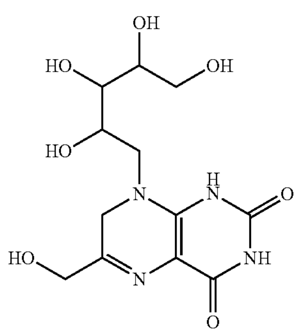

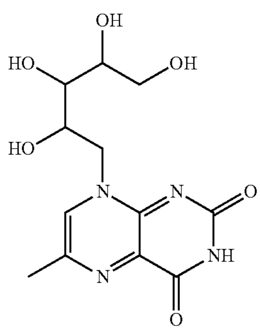

In another embodiment the compound of formula (Ia) is represented by one of the following formulae:

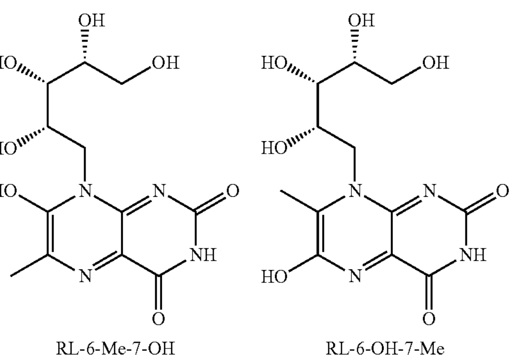

-continued

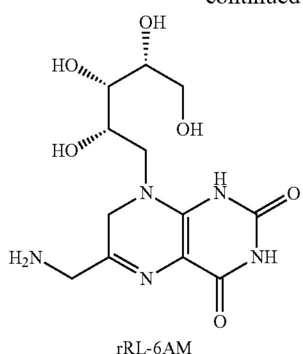

rRL-6AM

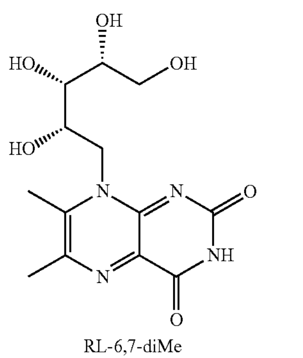

RL-6,7-diMe rRL-6HM

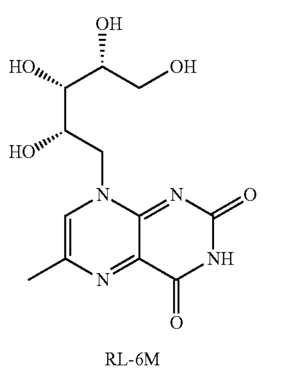

RL-6M

In an embodiment the compound is

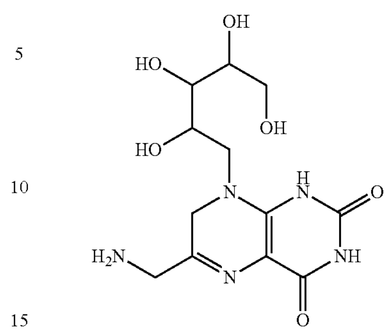

In a further embodiment the compound is:

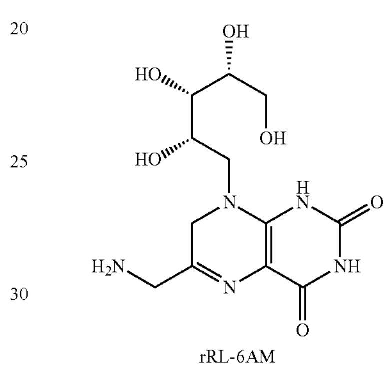

rRL-6AM

In an embodiment the ligand is represented by formula (II):

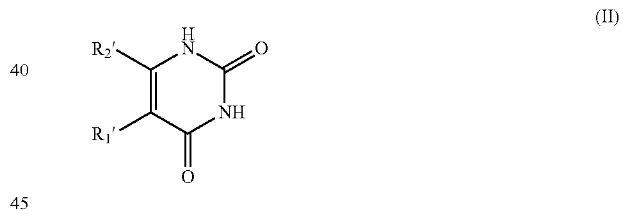

or salts, solvates, tautomers or stereoisomers thereof wherein:

$R_1$' is NO, $NH_2$, or NH (optionally substituted $C_{1-4}$ alkyl); and $R_2$' is NH (optionally substituted $C_{1-4}$ alkyl), N (optionally substituted $C_{1-4}$ alkyl) (optionally substituted acyl), NH (optionally substituted $C_{1-4}$ alkyl)$_2$.

In certain embodiments, $R_2$' is selected from:

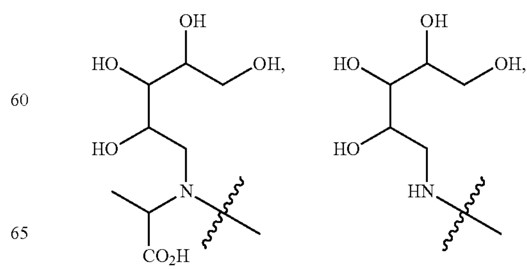

-continued

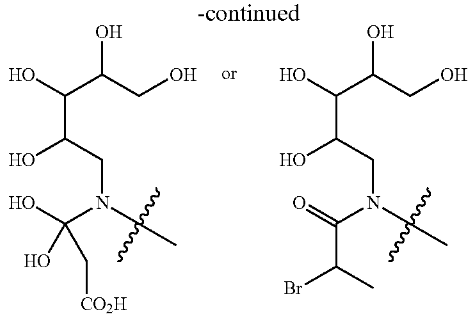

In certain embodiments $R_1'$ is selected from:

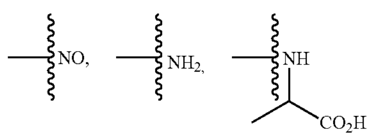

In one embodiment the ligand is:

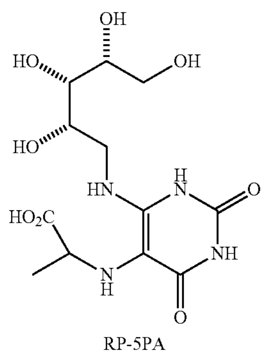 [SMILES: CC(Nc1c(NC[C@H](O)[C@H](O)[C@H](O)CO)[nH]c(=O)[nH]c1=O)C(=O)O]

Figure 2:
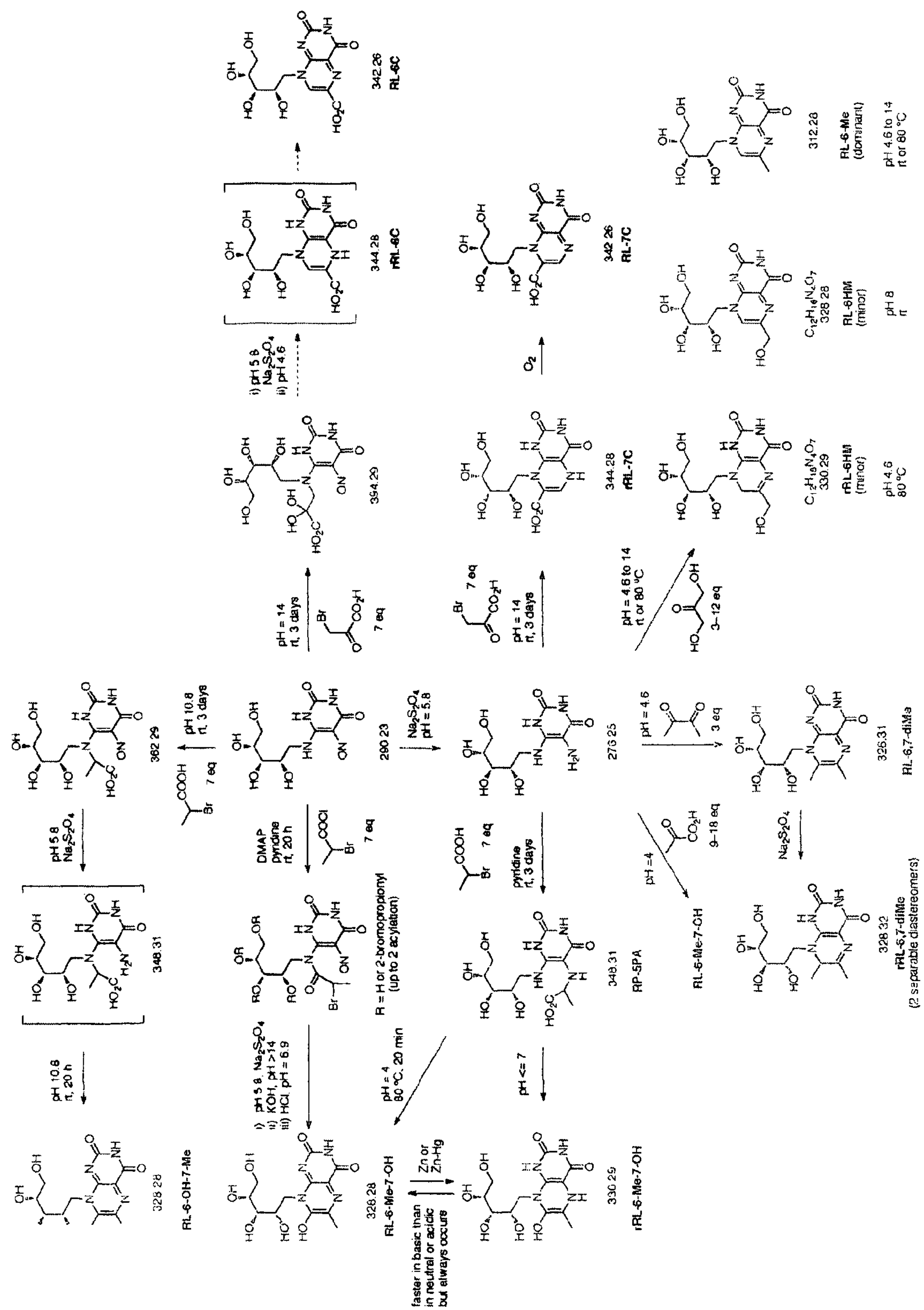
FIG. 2 is a schematic representation showing the synthetic route to the ligands of the invention.

The preparation of said compounds is outlined in FIGS. 1 and 2.

In an embodiment the ligand is a compound selected from the list consisting of rRL-6AM, rRL-6HM, RL-6M, RP-5PA, 6-formyl pterin, acetyl-6-formyl pterin or functional analogues thereof or 6-methyl-7-hydroxy-8-ribityl lumazine, 6-,7-dimethyl-8-Ribityl Lumazine or functional analogues thereof including oxidised and reduced forms thereof. In an embodiment the agent is the rRL-6HM.

The term "biological sample" as used herein includes but is not limited to a biological fluid (for example serum, lymph, blood), cell sample, or tissue sample (for example bone marrow or tissue biopsy including mucosal tissue such as from the gut, gut lamina propria, or lungs).

The terms "mammal", "mammalian" or "subject" as used herein includes humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). In an embodiment, the mammal or subject is human or other primate or a mouse.

In an embodiment, the MR1-ligand subunit or multimeric complex thereof forms a basis for the generation of mAbs, or engineered variants of mAbs, that specifically bind the MR1-ligand subunit or multimeric complex thereof. In an embodiment, the antibodies are bound with the activating agent for the purpose of detecting the MR1-agent complexes and/or blocking or enhancing their recognition by MAIT cells.

In a related aspect the present invention also provides a basis for generating mAbs, or engineered variants thereof, that specifically detect activating and non-activating MR1 ligands allowing their detection, quantitative estimation, blockade or enhancement.

The ability of the MR1-ligand subunit or multimeric complex thereof to interact with MR1 and to either inhibit or stimulate the activation of MAIT cells also makes them useful for the diagnosis, treatment or prevention of diseases or conditions, including, but not limited to, mucosal immune disorders and/or disorders associated with insufficient or excessive MAIT cell activity.

Reference to excessive MAIT cell activity should be understood as a reference to overactive cellular activity, or to physiologically normal cellular activity which is inappropriate in that it is unwanted.

In an embodiment, the ability of the MR1-ligand subunit or multimeric complex thereof to interact with MR1 and activate human MAIT cells makes them useful for, increasing MAIT cell activity in subjects having a disease or condition in which increased MAIT cell activity is beneficial, including those caused or characterized by insufficient MAIT cell activity.

It will also be appreciated that the MR1-ligand subunit or multimeric complex thereof are useful for decreasing MAIT cell activity in subjects having a disease or condition in which decreased MAIT cell activity is beneficial, including those caused or characterized by excessive MAIT cell activity.

In an embodiment, the MR1-ligand subunit or multimeric complex thereof are used to treat or prevent cancer, an infectious disease, an immune disease involving the mucosa, such as but not limited to Crohn's Disease, ulcerative colitis, irritable bowel disease, Multiple Sclerosis, chronic fatigue syndrome, oral infections, peptic ulceration, intestinal helminth or bacterial infection, ocular disease such as Trachoma, pelvic inflammatory disease, sexually transmitted diseases, Chlamydia infection, candidiasis and other fungal infections at epithelial and mucosal sites, tuberculosis or Celiac disease.

In another aspect, the present invention provides a pharmaceutical composition comprising the MR1-ligand subunit or multimeric complex thereof as hereinbefore described in an amount effective to detectably modulate MAIT cell activity in a subject or in a biological sample comprising MAIT cells.

In an embodiment the ligand is represented by formula (I):

(I)

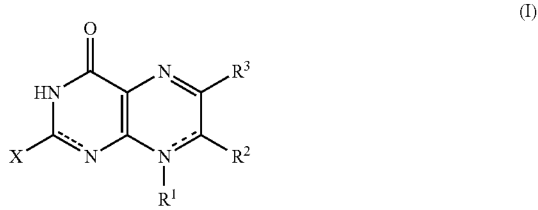

wherein:

X is selected from the list consisting of hydroxyl, oxo, amino, mono-$C_1$-$C_3$alkylamino or di-$C_1$-$C_3$alkylamino;

$R^1$ is present or absent and is selected from the list consisting of hydrogen, optionally substituted aryl, optionally substituted heteroaryl, and optionally substituted $C_1$-$C_{10}$alkyl;

$R^2$ and $R^3$ are each independently selected from the list consisting of hydrogen, halogen, halo $C_1$-$C_3$alkyl, optionally substituted $C_1$-$C_3$alkoxy, optionally substituted aryl, optionally substituted heteroaryl, and optionally substituted $C_1$-$C_3$alkyl; and --- represents an optional double bond;

or a pharmaceutically acceptable salt, solvate, or hydrate thereof, or a tautomer or stereoisomer thereof, in any isomeric ratio, including racemates and enantiomerically enriched mixtures.

With reference to formula (I), the optional substituents include but are not limited to a group selected from may be selected from the list consisting of halogen, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —N($C_1$-$C_4$alkyl)$_2$, —CN, —$NO_2$, mercapto, —$S(O_2)NH_2$, —$S(O_2)NHC_1$-$C_4$alkyl and $CO_2H$.

In an embodiment, said ligand is a compound selected from the list consisting of rRL-6HM, rRL-6AM, RL-6M, RP-5PA, 6-formyl pterin or acetyl-6-formyl pterin or 6-methyl-7-hydroxy-8-ribityl lumazine, 6-7-dimethyl-8-ribityl lumazine or functional analogues thereof including oxidised and reduced forms thereof. In one embodiment, the composition further comprises a pharmaceutically acceptable carrier or excipient. In an embodiment the agent is rRL-6HM.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

In another aspect, the present invention provides use of the MR1-ligand subunit or multimeric complex thereof, or compositions comprising said MR1-ligand subunit or multimeric complex thereof in the manufacture of a medicament for the treatment or prophylaxis of a disease condition in a subject in need thereof.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

In other embodiments, the methods described herein may comprise the additional step of administering to said subject an appropriate additional therapeutic agent selected from an immunomodulatory agent, a hormonal agent, a chemotherapeutic agent, an anti-angiogenic agent, an apoptotic agent, a second antibody that binds to and modulates a MAIT cell receptor, an anti-infective agent, a targeting agent, an anti-inflammation drug, a steroid, an immune system suppressor, an antibiotic, an anti-diarrheal drug, or an adjunct compound. Such additional agents can be administered to said patient as a single dosage form together with the agents of the invention as hereinbefore defined, as a separate dosage form.

The herein described MR1-ligand subunit or multimeric complex thereof, or compositions comprising same can be included in kits, as diagnostic reagents for detecting the presence of MAIT cells. It will be appreciated that, the kit may contain other types of therapeutic compounds as well, such as other anti-inflammatory agents. Preferably, the kits also include instructions for using the MR1-ligand subunit or complex comprising two or more subunits, for example, detailing the herein-described methods.

The dosage of agent of the invention used in accordance with the methods of the invention are sufficient to detectably induce, promote, and/or enhance a therapeutic response in the subject.

Pharmaceutically acceptable carriers that may be used in compositions comprising the agent of the invention, include but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of this invention may be employed in a method of modulating, for example enhancing or inhibiting, the activity of MAIT cells in a subject or a biological sample. This method comprises the step of contacting said composition with said patient or biological sample. Such method will be useful for both diagnostic and therapeutic purposes.

The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, for example, lactose. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation. Patches may also be used.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

According to another embodiment, the compositions of this invention may further comprise another therapeutic agent, including agents normally utilized for the particular therapeutic purpose for which the composition is being administered. The additional therapeutic agent will normally be present in the composition in amounts typically used for that agent in a monotherapy for the particular disease or condition being treated. Such therapeutic agents include, but are not limited to, therapeutic agents used in the treatment of cancers, therapeutic agents used to treat infectious disease, therapeutic agents used in other immunotherapies, cytokines (such as IL-2 or IL-15), anti-inflammation agents, steroids, immune system suppressors, antibiotics, anti-diarrheal drugs, and other antibodies and fragments thereof.

The methods of the present invention may be combined with any other methods generally employed in the treatment of the particular disease, such as immune disorders involving the mucosa. So long as a particular therapeutic approach is not known to be detrimental to the subjects condition in itself, and does not significantly counteract the activity of the agents or compositions of the invention, its combination with the present invention is contemplated.

When one or more additional therapeutic agents are used in combination with an agent or composition of this invention in a therapeutic regimen, there is no requirement for the combined results to be additive of the effects observed when each treatment is conducted separately. Although at least additive effects are generally desirable, any increased effect above one of the single therapies would be of benefit. Also, there is no particular requirement for the combined treatment to exhibit synergistic effects, although this is certainly possible and advantageous.

In connection with solid tumor treatment, the agents or compositions of the present invention may be used in combination with classical approaches, such as surgery, radiotherapy, chemotherapy, and the like. The invention therefore provides combined therapies in which a pharmaceutical composition of this invention is used simultaneously with, before, or after surgery or radiation treatment; or are administered to patients with, before, or after conventional chemotherapeutic, radiotherapeutic or anti-angiogenic agents, or targeted immunotoxins or coaguligands.

In other aspects, immunomodulatory compounds or regimens may be administered in combination with or as part of the agents or compositions of the present invention. Preferred examples of immunomodulatory compounds include cytokines. Various cytokines may be employed in such combined approaches. Examples of cytokines useful in the combinations contemplated by this invention include IL-2, IL-3, IL-4, IL-5, IL-6, IL-7, IL-8, IL-9, IL-10, IL-12, IL-13, IL-15, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, and IFN-beta. Cytokines used in the combination treatment or compositions of this invention are administered according to standard regimens, consistent with clinical indications such as the condition of the patient and relative toxicity of the cytokine.

The present compositions can also be administered in conjunction with anti-inflammatory agents, such as NSAIDS, aspirin, salsalate, diflunisal, ibuprofen, ketoprofen, nabumetone, piroxicam, naproxen, diclofenac, indomethacin, sulindac, tolmetin, etodolac, ketorolac, oxaprozin, celecoxib, corticosteroids, oral steroids, prednisone, prednisolone, beclomethasone, fluticasone, budesonide, betamethasone, dexamethasone, aclomethasone and clobetasone.

It will be appreciated that the ligands can be used for the identification of further ligands for the purpose of blocking or activating MAIT cells or generating multimer MR1-ligand reagents, for example tetramers, for detection, monitoring or immunotherapy directed towards MAIT cells.

A non-limiting example of this further aspect of the invention involves the use of combinatorial chemistry employing 6-formyl pterin, acetyl-6-formyl pterin or functional analogues thereof, or a compound selected from the list consisting of rRL-6AM, rRL-6HM, RL-6M, RP-5PA, 6-methyl-7-hydroxy-8-ribityl lumazine, 6-,7-dimethyl-8-ribityl lumazine or functional analogues thereof including but not limited to oxidised and reduced forms thereof used as the scaffold basis for identification of further ligands for the purpose of blocking or activating MAIT cells or generating multimer MR1-ligand reagents.

Without limiting the application of the present invention in any way, the method of the present invention facilitates the analysis, design and/or modification of ligands capable of interacting with MR1 and forming a complex which either inhibits or promotes the interaction of MR1 with MAIT cells. In this regard, reference to “analysis, design and/or modification” of an agent should be understood in its broadest sense to include:

(i) Randomly screening (for example, utilising routine high-throughput screening technology) to identify agents which exhibit some modulatory capacity with respect to MAIT cell activity and then analysing the precise nature and magnitude of the ligands modulatory capacity utilising the method of this aspect of the present invention. In this regard, existing crystals could be soaked with said agents or co-crystalisation could be performed. A combination of modelling and synthetic modification of the local compound together with mutagenesis of the MR1 binding site could then be performed for example. In screening for agents which may modulate activity, standard methods of phage display and also combinatorial chemistry may be utilised (Goodson et al., 1994; Terrett., 2000). Such interaction studies can also be furthered utilising techniques such as the Biacore analysis and NMR perturbation studies. Such agents are often commonly referred to as “lead” agents in terms of the random screening of molecules for their capacity to function either agonistically or antagonistically. Further, for example, binding affinity and specificity could be enhanced by modifying lead agents to maximise interactions with the MR1 binding site. Such analyses would facilitate the selection of agents which are the most suitable for a given purpose. In this way, the selection step is based not only on in vitro data but also on a technical analysis of sites of agent: MR1 interaction in terms of their frequency, stability and suitability for a given purpose. For example, such analysis may reveal that what appears to be an acceptable in vitro activity in respect of a randomly identified agent is in fact induced by a highly unstable interaction due to the presence of proximally located agent: MR1 sites which exhibit significant repulsive forces thereby de-stabilising the overall interaction between the agent and the MR1. This would then facilitate the selection of another prospective lead compound, exhibiting an equivalent degree of in vitro activity, but which agent does not, upon further analysis, involve the existence of such de-stabilising repulsive forces.

Screening for the modulatory agents herein defined can be achieved by any one of several suitable methods, including in silico methods, which would be well known to those of skill in the art and which are, for example, routinely used to randomly screen molecules for the purpose of identifying lead compounds.

These methods provide a mechanism for performing high throughput screening of putative modulatory agents such as the agents comprising synthetic, recombinant, chemical and natural libraries.

(ii) The candidate or lead agent (for example, the agent identified in accordance with the methodology described in relation to point (i)) could be modified in order to maximise desired interactions (for example, binding affinity to specificity) with MR1 and to minimise undesirable interactions (such as repulsive or otherwise de-stabilising interactions).

Methods of modification of a candidate or lead agent in accordance with the purpose as defined herein would be well known to those of skill in the art. For example, a molecular replacement program such as Amore (Navaza, 1994) may be utilised in this regard.

(iii) In addition to analysing fit and/or structurally modifying existing molecules, the method of the present invention also facilitates the rational design and synthesis of an agent, such as an agonistic or antagonistic agent, based on theoretically modelling an agent exhibiting the desired MR1 binding site interactive structural features followed by the synthesis and testing of the subject agent.

It should be understood that any one or more of applications (i)-(iii) above, may be utilised in identifying a particular agent.

Certain embodiments of the invention will now be described with reference to the following examples which are intended for the purpose of illustration only and are not intended to limit the scope of the generality hereinbefore described.

EXAMPLES

Methods

Preparation of Denatured Inclusion Body MR1 and β2m Protein

The method for refolding and purifying MR1-β2m-ligand complex is based on a similar methodology used for classical MHC heavy chain-β2m-peptide complex described in Garboczi et al. 1992. Genes encoding soluble human MR1 (residues 1-270 of the mature, leaderless protein, lacking the transmembrane and cytoplasmic domains); or human β2m (mature, leaderless protein) were expressed for four hours in BL21 *E. coli* following induction with 1 mM isopropyl β-D-1-thiogalactopyranoside. *E. coli* were pelleted and resuspended in a buffer containing 50 mM Tris, 25% (w/v) sucrose, 1 mM EDTA, 10 mM DTT pH 8.0. Inclusion body protein was then extracted by lysis of bacteria in a buffer containing 50 mM Tris pH 8.0, 1% (w/v) Triton X-100, 1% (w/v) sodium deoxycholate, 100 mM NaCl, 10 mM DTT, 5 mM $MgCl_2$, and 1 mg DnaseI per liter of starting culture; and subsequent steps involved homogenization with a polytron homogenizer, centrifugation, and washing inclusion body protein sequentially with firstly a buffer containing 50 mM Tris pH 8, 0.5 5 Triton X-100, 100 mM NaCl, 1 mM EDTA, 1 mM DTT, and secondly a buffer containing 50 mM Tris pH 8.0, 1 mM EDTA, 1 mM DTT. Inclusion body protein was then resuspended in a buffer containing 20 mM Tris pH 8.0, 8 M urea, 0.5 mM EDTA, 1 mM DTT, and following centrifugation the supernatant containing solubilized, denatured inclusion body protein was collected and stored at −80° C.

Refolding of MR1 and β2m with Ligands 2 mg of 6-formyl pterin, 56 mg of denatured inclusion body MR1 protein, and 28 mg of β2m protein were added to a 400 ml refold buffer solution containing 0.1 M Tris pH 8.5, 2 mM EDTA, 0.4 M arginine, 0.5 mM oxidized glutathione, 5 mM reduced glutathione. Variably, 5M urea was either present or absent. Following an overnight incubation at 4° C., the refold buffer was dialysed against 3 changes of buffer containing 10 mM Tris, pH8.0 over a period of 24 hours. Refolded MR1-β2m-ligand complex was then purified by sequential DEAE (GE Healthcare) anion exchange, S75 16/60 (GE Healthcare) gel filtration, and MonoQ (GE Healthcare) anion exchange chromatography.

Analysis of Refolded MR1-β2m-Ligand Complex by Mass Spectrometry 4 mg MR1-β2m-6-formyl pterin complex (or complex obtained by refolding MR1 with b2m and *Salmonella* supernatant) was loaded unto an XBridge C18 reversed phase column (Waters) using 20 mM NH4acetate pH 5.4 buffer, and eluted using a gradient of acetonitrile, unto an Agilent electrospray ionization time-of-flight (ESI TOF) mass spectrometer. Data was collected in negative mode. 0.4 mg of control 6-formyl pterin was analysed in a similar manner. Data was analysed using the Agilent MassHunter software. Mass-to-charge (m/z) species specifically associated with refolded MR1-β2m-ligand complex was subjected to targeted fragmentation on an Agilent Q TOF mass spectrometer. MS MS fragmentation products were analysed against the Scripps Metlin Metabolite MS database.

Crystallization, Structure Determination, and Refinement

MR1 (5-10 mg/ml) crystallized at room temperature in 0.02M MgCl2, 0.1M HEPES pH 7.5 and 22% polyacrylic acid 5100 sodium salt. Equal ratio of the protein to mother liquor resulted in plate-like crystals. The crystals were improved by seeding into 0.2M NaCl, 0.1M HEPES pH 7.5, 25% PEG 3350. Crystals were flash frozen prior to data collection using 35% PEG3350 as the cryoprotectant. The data was collected at 100K on the 031D1 beamline at the Australian Synchrotron, Melbourne. The crystals of MR1 diffracted to 3.2 Å and belong to the space group $P2_12_12_1$, with two molecules within the asymmetric unit. The data was processed using Mosflm version 7.0.5 (Leslie, A. G. W. (1992)) and scaled using SCALA from the CCP4 Suite (CCP4, 1994; Vagin and Teplyakov, 1997). The data was solved by the molecular replacement method using MOLREP in CCP4, with HLA-G (PDB code 1YDP) without the peptide and loop region as a search model. The structure was refined using BUSTER 2.10 (Bricogne et al., 2011). Model building was carried out using COOT (Emsley and Cowtan, 2004). The ligand was modeled using the Dundee PRODGR2 server (Schuttelkopf and van Aalten, 2004). The overall structure was validated using MOLPROBITY (Davis et al., 2007). All molecular graphics representations were created using PyMOL (DeLano, 2002). Surface area calculations were done using the Protein interfaces, surfaces and assemblies service PISA at European Bioinformatics Institute (http://www.ebi.ac.uk/pdbe/prot_int/pistart.html) (E. Krissinel and K. Henrick J. Mol. Biol 2007). Cavity volumes were calculated using Pocket Finder (Hendlich et al., 1997).

Synthesis of MR1 Ags

Compounds 6,7-dimethyl-8-D-ribityllumazine (1), 7-hydroxy-6-methyl-8-D-ribityllumazine (2) and a 2 electron reduced form (3) of 6-hydroxymethyl-8-D-ribityllumazine were synthesised by modifications (FIG. 64) to reported literature procedures (for review see Plaut et al 1974). Their purities were established using proton NMR spectra and reversed phase HPLC traces. In brief, D-ribitylamine (6) was produced in 55% yield from D-(−)-ribose via its oxime intermediate. Condensation with 4-chlorouracil (7) followed by nitrosation provided the key intermediate (9) in reasonable yield (27%). The diaminouracil (10) was unstable, and therefore it was generated in situ, immediately before use, by reduction of the nitroso group with sodium hydrosulfite. Condensation with the corresponding α,β-dicarbonyl reagents at the optimal pH under a nitrogen atmosphere in the dark gave the products 1 and 2 after purification by preparative HPLC. The amount of α,β-dicarbonyl reagents significantly affected the product profiles. For dimethyl analogue 1, three equivalents of 2,3-butadione gave a much purer crude product than reported in the literature, in which 6.6 equivalents gave a significant amount of bis-adduct and made purification difficult. Compound 1 was unstable, particularly in solution. Thus prolonged reaction and work-up procedures were best avoided. In contrast, a large excess of sodium pyruvate (9-18 eq) was key for efficient production of the 7-hydroxy analogue. Similarly, condensation with excess 1,3-dihydroxyacetone dimer (a reduced form of α,β-dicarbonyl) gave directly the reduced derivative 3 in low yield (5%), which was identified by NMR spectra (1H, 13C, COSY, HSQC in DMSO-d6-D2O 10:1, v/v) with characteristic resonances for 6-hydroxymethyl (1H/13C: δ 5.27, singlet/80.0) and reduced ring methylene at position-7 (1H/13C: δ 4.16 and 4.03, AB quartet, J=13.7 Hz/62.6). The reduced derivative of RL-6,7-diMe (4) was prepared using excess sodium hydrosulfite (5 eq) and easily desalted and separated from the starting material using a cation-exchange column (Amberlite IR-120, H+ form). However, this reduced form 4 was readily oxidised by air and rapidly reverted to the original state 1. Two diastereomers of 4 were partially separated using preparative rpHPLC to give enriched diastereomers (92:8 and 91:9), which were identified by NMR spectra (1H, 13C, COSY, HSQC) with characteristic cross-coupled signals between the 7-methyl group (1H/13C: δ 1.16, doublet, J=6.8 Hz/14.4 and δ 1.17, doublet, J=6.8 Hz/13.4) and the 7-methine CH (1H/13C: δ 4.35, quartet/57.8 and δ 4.31, quartet/55.5).

Activation of Jurkat.MAIT Cells

Jurkat cells transduced with a MAIT TCR comprising the TRAV1-2+TRAJ33 invariant α chain, and a TRBV6-1 β chain were tested for activation by addition of *Salmonella* supernatant to C1R antigen presenting cells expressing MR1 for 16 hours. Jurkat.MAIT cells were subsequently stained with PE-conjugated anti-CD3, and APC-conjugated anti-CD69 antibodies before analysis by flow cytometry. Activation of Jurkat.MAIT cells was measured by an increase in surface CD69 expression. Compounds to be tested for the ability to activate Jurkat.MAIT cells were tested alongside *Salmonella* supernatant.

Activation of MAIT Cells

PBMCs from a healthy donor were mixed with C1R-huMR1 cells ($10^5$ each/well). *Salmonella* SL1344 supernatant (2 μl) from cultures grown in LB supplemented with 25 μg/ml streptomycin (Sigma) for 4 hr at 37° C., or compounds (35A, 36A, 48G: 25 μg/ml final, A-6FP: 10 μM final) or PMA (2 ng/ml+ionomycin (1 ng/ml) added in a total volume of 220 μl RF-10, and incubated overnight at 37° C. Cells were stained with anti-CD3-PE-Cy7 (eBioscience, 20 μg/ml), anti-CD4-APC-Cy7 (Biolegend, 1.7 μg/ml), anti-CD161-APC (Miltenyi Biotec, 1:50), FITC-conjugated D5 (anti-MAIT TCR, 10 μg/ml) and either anti-CD69-PE (BD Biosciences 1:50), anti-IFNγ-PE (BD Pharmingen 10 μg/ml) or anti-TNFα-PE (BD Pharmingen 10 μg/ml), and analyzed by flow cytometry using a Canto II cytometer and Diva software. For intracellular cytokine staining, brefeldin A (10 μg/ml) was added to the assay after the first 1 hr and the incubation allowed to proceed overnight. Cells were fixed with 1% parformaldehyde after staining for surface markers and permeabilised with 1% saponin during cytokine stains. MAIT cells were defined as $CD3^+$, $CD4^-$, $CD161^+$, $D5^+$ after gating on PBMCs using FSC and SSC.

Specific Activation of Primary MAIT Cells, but not Non-MAIT Cells by RL Compounds PBMCs from a healthy donor were mixed with C1R cells expressing MR1 ($10^5$ each/well). *Salmonella* SL1344 supernatant (2 μl) from cultures grown in LB supplemented with 25 μg/ml streptomycin (Sigma) for 4 hr at 37° C., or compounds (RL-6,7-diMe, RL-6-Me-7-OH, 6FP: 76.2 μM final, rRL-6-HM: 0.152 μM final) or PMA (2 ng/ml+ionomycin (1 ng/ml) added in a total volume of 220 μl RF-10, and incubated overnight at 37° C. Cells were stained with anti-CD3-PE-Cy7 (eBioscience, 20 μg/ml), anti-CD4-APC-Cy7 (Biolegend, 1.7 μg/ml), anti-CD161-APC (Miltenyi Biotec, 1:50), FITC-conjugated D5 (anti-MAIT TCR, 10 μg/ml) and either anti-CD69-PE (BD Biosciences 1:50), anti-IFNγ-PE (BD Pharmingen 10 μg/ml) or anti-TNFα-PE (BD Pharmingen 10 μg/ml), and analyzed by flow cytometry using a Canto II cytometer and Diva software. For intracellular cytokine staining, brefeldin A (10 μg/ml) was added to the assay after the first 1 hr and the incubation allowed to proceed overnight. Cells were fixed with 1% parformaldehyde after staining for surface markers and permeabilised with 1% saponin during cytokine stains. MAIT cells were defined as $CD3^+$, $CD4^-$, $CD161^+$, $D5^+$ after gating on PBMCs using FSC and SSC. PBMCs were mixed with C1R cells expressing MR1 ($10^5$ each/well) and *Salmonella* supernatant (Salm. S/N; 2 μl); or compounds (RL-6,7-diMe, RL-6-Me-7OH, 6FP: 76.2 μM final, rRL-6-HM: 0.152 μM final); or PMA and ionomycin (PMA/Ion; 2 ng/ml and 1 ng/ml respectively) in 220 μl RF-10 and incubated overnight at 37° C. CD69 expression was analysed by flow cytometry. After 1 hr incubation, 10 μM brefeldin A was added and cells incubated overnight. Cells were stained for surface markers, fixed in 1% paraformaldehyde and permeabilised with 1% saponin prior to intracellular cytokine staining.

Targeted Enzymatic Conjugation of Biotin to Peptide-Tagged MR1:

BirA-tagged MR1 (containing the C-terminal sequence: SGLVPRGSHMLHHILDAQKMVWNHRHHHHHH) is refolded and purified by anion-exchange chromatography and gel filtration, before it is subsequently buffer exchanged into 10 mMTris (pH 8.0) using a PD-10 column (GE Healthcare). Protein is eluted in a final volume of 3.5 ml and concentrated with a VIVASPIN 6 (Sartorius) centrifugal concentrator to a volume of 100-200 ul, and was then biotinylated with biotin ligase (BirA enzyme; Avidity) in a reaction mix (as below) overnight in the dark at room temperature.

| | Reaction Mix 1x | Prepared volume (μl) |
|---|---|---|
| Biomix A (10x concentration: 0.5M bicine buffer, pH 8.3) | 1/10 dilution | 100 |
| Biomix B (10x concentration: 100 mM ATP, 100 mM MgOAc, 500 μM d-biotin) | 1/10 dilution | 100 |
| PMSF (500x) | 1/500 dilution | 2 |
| Pepstatin A (1000x) | 1/1000 dilution | 1 |
| Total Volume | n/a | 203 |
| Substrate- AviTagged protein monomers | (1/1.25 dilution) | — |
| BirA enzyme (1 mg/ml) | Use 2.5 ug per mg of protein to be biotinylated* | — |

Excess biotin is removed from biotinylated MR1 by S200 10/300 GL gel filtration chromatography (GE Healthcare), using Tris buffered saline (pH 8.0). Eluted protein was then concentrated to 100-200 μl in a VIVASPIN 6 (Sartorius) centrifugal concentrator.

Chemical Biotinylation with Sulfhydryl-Reactive Biotin to Cysteine-Tagged MR1:

MR1 with the addition of a C-terminal cysteine, is refolded and subsequently purified by standard anion exchange and gel filtration chromatography methods. MR1 is then reduced in 5 mM DTT for 15 min at room temperature and buffer exchanged into PBS using a PD-10 column (GE Healthcare), and concentrated in a VIVASPIN 6 (Sartorius) centrifugal concentrator to 200 μl. Cysteine-tagged MR1 is then biotinylated with Maleimide-PEG2 biotin (Thermoscientific) at a 30:1 molar excess of biotin:protein at 4° C. in the dark overnight. Excess biotin is removed by passing biotinylated protein through an S200 10/300 GL (Healthcare) gel filtration column in Tris buffered saline (pH 8.0).

Biotinylated MR1 (produced in either of the 2 methods mentioned above) is used to make tetramers by the addition of biotinylated MR1 to PE Streptavidin (#554061, BD Pharmingen) in a 4:1 molar ratio. PE Streptavidin is added sequentially in 1/10 aliquots to biotinylated MR1 at 10 minute intervals to ensure efficient tetramization.

Example 1

Activation of MAIT T Cell Receptor (TCR)-Expressing T Cell Lines by Antigen Presenting Cells A biological assay for the activation of MAIT T cell receptor (TCR)-expressing T cell lines (into which genes encoding the MAIT TCR alpha and beta chains had been introduced), by antigen presenting cells (expressing MR1 on the cell surface) infected with the bacterium *Salmonella typhimurium* has been established. This assay measures the increase in expression of the cell surface activation marker, CD69, upon activation of MAIT T cells. Activation can be blocked with an MR1-specific monoclonal antibody, 26.5, thus demonstrating the specificity of the interaction between the MAIT TCR (on the T cell), and MR1 (on the antigen presenting cell).

It was subsequently discovered that 0.2 micron-filtered supernatant from *S. typhimurium* is similarly capable of activating MAIT T cells. That is, activation of MAIT T cells can occur in the absence of infection by *S. typhimurium* bacteria.

Further characterization of this supernatant by size exclusion chromatography revealed that the active species appears to have a molecular weight smaller than the classical MHC-bound viral peptide FLRGRAYGL (1,051 daltons).

Denatured, soluble MR1 (expressed in *E. coli*) was demonstrated, in the presence of β2m and 0.2 micron-filtered supernatant from *S. typhimurium*, to be refolded into its native conformation.

The refolded MR1 binds to an MR1-specific monoclonal antibody, 26.5 (as demonstrated by ELISA); has a size exclusion chromatography retention time very similar to the retention times of classical MHC molecules; and exhibits a 1:1 stoichiometry with the associated β2m (similar to the 1:1 stoichiometry observed for classical MHC and β2m).

Adding the refolded, soluble MR1 (but not a control refolded soluble classical MHC molecule) to antigen presenting cells expressing MR1 and MAIT cells, resulted in activation of the MAIT cells.

Two key control experiments were performed: First, refolding MR1 with no added *S. typhimurium*, results in a dramatic decrease in recovered refolded MR1, which lacked ability to activate MAIT T cells in the assay described above.

Secondly, if MR1 was refolded in the presence of RPMI medium (the nutrient medium for *S. typhimurium* prior to harvest of supernatant-containing activity), there was a significant (though decreased) yield of recovered, refolded MR1. This refolded MR1 lacked activity in the re-presentation assay described above.

Analysis of RPMI shows that it is composed of inorganic salts, amino acids, vitamins, and other miscellaneous ingredients such as D-glucose, glutathione, and phenol red (Table 2).

Example 2

Identifying Inactive MR1-Bound Ligand

Whether the inactive MR1-bound ligand (capable of enabling denatured MR1 to be refolded into native MR1) may be a vitamin or vitamin-derivative; and whether the active MR1-bound ligand may be a biochemically modified product of the same vitamin or vitamin-derivative was assessed.

MR1 was refolded with an independent and more plentiful source of the different vitamins found in RPMI medium: Nature's Own Super B™ complex tablets. Five tablets were dissolved in the standard refold buffer; MR1 refolded in significant yields in the presence of Super B complex tablets, compared to the "nil additive" control. This refolded MR1 failed to activate MAIT cells in a re-presentation assay.

Individual vitamin B components were then tested in refolds with MR1. Folic acid, when added to MR1 refolds, yielded significant amounts of native MR1. MR1 refolded with folic acid however failed to activate MAIT cells in a re-presentation assay.

Mass spectrometry experiments were conducted with refolded MR1, in order to try and identify the MR1-bound ligand. These experiments include: analysis of refolded MR1 by electrospray ionization time-of-flight (ESI TOF) mass spectrometry, which has revealed that in negative mode, two m/z species of 190.03 and 147.03 were detected with identical retention times on an SGE C8 1000A reversed phase column. These species were absent in control blank and classical MHC analyses.

A search of the Scripps Metlin data bank revealed that biopterin (mass 237.0862) upon mass spectrometry analysis in negative mode yielded m/z fragment species of 190.03 and 147.03. Biopterin contains a core pterin moiety.

ESI TOF MS, with two MR1-specific m/z species of identical retention times, and the Scripps Metlin data bank results demonstrated the common ancestry of 2 species with identical m/z values to those which were identified from MR1, suggest that a pterin-containing compound is specifically associated with MR1. Folic acid contains the pterin moiety, as well as p-aminobenzoate and glutamate.

Further analysis by ESI TOF mass spectrometry of folic acid, along with MR1 refolded with folic acid, was performed. Although an m/z species of 440.17 (440.17 is consistent with the theoretical [M-H]—m/z of 440.13 of folic acid, as the ESI TOF instrument was not accurately calibrated for this experiment), was readily detected with the starting folic acid compound; in contrast MR1 refolded with folic acid yielded m/z species of 190.07 and 147.065 (in this experiment again erring from 190.03 and 147.03), but the 440.17 species could not be detected.

Thus, a compound which shares an identical m/z value with 6-formyl pterin has been identified which bind to MR1; and since MR1 refolded with folic acid is non-stimulatory to MAIT T cells. MR1 which was refolded with 6-formyl pterin purchased from Schircks Laboratories (product #11.415) was indistinguishable from MR1 refolded with folic acid, as determined by gel filtration and MonoQ anion exchange chromatography, and by SDS-PAGE of purified MR1; and identical m/z 190.03 species were identified from MR1 refolded by both 6-formyl pterin and folic acid.

In a control experiment, 6-formyl pterin was shown to have no inhibitory effect on the activation of Jurkat cells expressing a conventional T cell receptor, by antigen presenting cells displaying viral peptide-classical class I complexes. Thus, 6-formyl pterin has been identified as a potential antagonist compound, capable of blocking activation of MAIT cells by bacterial activating ligands.

This finding correlated well with the inability (6-7-dimethylpterin and pterin), and greatly diminished ability (6-hydroxymethylpterin) of control pterin compounds to refold with MR1. Subsequent ESI TOF mass spectrometric analysis of MR1 refolded with 6-hydroxymethylpterin demonstrated that the small yields of refolded MR1 in this instance contained 6-formyl pterin. Thus, trace contaminant of 6-formyl pterin, present in preparations of 6-hydroxymethylpterin, was what enabled small amounts of MR1 to be refolded in this instance.

Example 3

The Structure of MR1-Ag

To gain insight into the detailed architecture of the MR1 molecule, MR1 was expressed and refolded MR1 in complex with 6-FP and subsequently determined the structure of the MR1-6-FP complex to 3.2 Å resolution, to an $R_{fac}$ and $R_{free}$ value of 19.3% and 25.8% respectively (Table 2). The electron density for the entire MR1-Ag complex was excellent and unambiguous, thereby permitting detailed structural analyses to be made to representative peptide- and lipid-binding Ag-presenting molecules, namely HLA-A2 and CD1d respectively.

The Ag-binding domain of MR1 adopts a standard MHC-I fold, with a heavy chain comprising three domains (α1, α2 and α3) non-covalently associated with β-2 microglobulin (β2m), which lies adjacent to the α3 domain and "underneath" the α1-α2 domains. The MR1 heavy chain shares close structural homology with HLA-A2 (39% sequence identity, root mean square deviation (r.m.s.d.) of 1.73 Å over 213 Cα atoms) and CD1d (22% sequence identity, r.m.s.d. 2.26 Å over 151 Cα atoms). A database search showed that MR1 was most closely related to an avian monomorphic MHC-I like molecule (43% sequence identity, rmsd 1.77 Å over 276 Cα atoms), that is thought to bind non-peptide based Ags (Hee et al. Plos Biol. 2010). The α1-α2 domains form the Ag-binding cleft of MR1, which comprises two long α-helices sitting atop a β-sheet, akin to HLA-A2 and CD1d. The helices of the MR1 Ag-binding cleft were not closely juxtaposed, as was observed for HFE, a receptor that adopts an MHC-1 like fold but does not bind Ag. Indeed, the positioning of the α1 and α2 helices of MR1 more closely resembled HLA-A2 than that of the more constricted CD1d Ag-binding cleft (r.m.s.d. 1.0 Å over 133 Cα atoms and 3.1 Å over 99 Cα atoms respectively). However, the central cleft of MR1 is neither suited, chemically or structurally, to accommodate peptide nor lipid-based Ags. For example, while the cleft of HLA-A2 is solvent exposed and mostly polar in nature, and CD1d comprises a hydrophobic-lined cavity mostly shielded from solvent, the Ag-binding cleft of MR1 is atypical in that it is solvent exposed, consisting of a mixture of charged and hydrophobic residues, of which a preponderance of aromatic residues within the α1 and α2 helices was evident. Further, the central cavity of MR1 is rather restricted, measuring 760 $Å^3$, whereas that of CD1d, at 1690 $Å^3$, is much larger. Moreover, while MHC-Ia comprises a conserved network of residues at the N- and C-terminal ends of the Ag-binding groove that tethers the termini of the antigenic peptide, the corresponding locations within the MR1 cleft, whilst showing some conservation, are different. However, the end of the MR1 groove is not “open”, as observed for MHC-II molecules. While MHC-Ia comprises six pockets that accommodate the side chains of the peptide, MR1 does not possess analogous “pockets”. Instead, a large number of bulky side chains occupy the entire length and breadth of the cleft, and it is this architecture that presumably prevents the helical jaws of MR1 closely packing together. Accordingly the structure of chemical properties of the MR1 Ag-binding cleft is distinct from that of peptide and lipid-Ag presenting molecules.

Mode of MR1-Ag Presentation

6-FP is located centrally within the MR1 cleft, equidistant from the α1 and α2 helices, and positioned towards the base of the β-sheet. The pterin ring lies relatively flat against the β-sheet, and is located differently to where abacavir, another dicyclic compound, has recently been established to bind HLA-B*5701 (Illing et al., Nature 2012). The pterin-based ligand exhibits very limited solvent accessibility, with 317 Å2 of the available 327 Å2 being buried by MR1. 6-FP is dominated by hydrophobic interactions, in which Tyr7, Tyr62, Trp69 and Trp156 act as an “aromatic cradle” that closely sequesters the ligand. In addition, the ligand forms vdw interactions with Arg 9, Arg 94, Ile 96 and Gln 153 (Table 2). There was evidence of a direct covalent bond between the NZ group of Lys43 and the formyl group of 6-FP, indicating that the Lys43 formed a Schiff's base with the formyl group. Adjacent to the MR1-Ag binding pocket was the location of two positively charged residues (Arg9 and Arg94), which protruded up into the cleft adjacent to the pterin ring, suggestive of the requirement of polar moieties for other potential MR1-restricted ligands. The residues involved in contact with 6-FP (and the two Arg residues) are conserved across MR1 from all species.

Example 4

Identifying Active MR1 Bound Ligand

High accuracy ESI TOF mass spectrometry allowed accurate determination of the mass-to-charge (m/z): 329.1094, permitting a tentative atomic composition of $C_{12}H_{18}N_4O_7$. An informatics search for a potential matching compound suggested 7-hydroxy-6-methyl-8-ribityl-lumazine, with an atomic composition C12H16N4O7. Thus the potential compound identified by mass spectrometry would be predicted to be a reduced form (C12H18N4O7) of 7-hydroxy-6-methyl-8-ribityl-lumazine.

Human MAIT cells have been shown to be xeno-reactive to mouse MR1 (Huang et al. PNAS, 2009). Thus at least a subpopulation of human PBMCs (D5-positive, CD161-positive cells, depending on source of patient PBMCs) were predicted to stain with mouse MR1 tetramers.

Tetramers of mouse MR1-β2m-acetyl-6-Formyl Pterin (mouse MR1 refolded with acetyl-6-formyl pterin) specifically stained human MAIT cells from human peripheral blood monocyte cells (PBMCs). Significantly, control tetramers of human MR1-β2m-acetyl-6-Formyl Pterin failed to bind any human PBMCs. Human MAIT cells are identified as being D5-positive (D5 mAb stains Vα7.2,-positive T cells; Vα7.2 is the invariant Vα-chain utilized by human MAIT cells) and CD161-positive. Human PBMCs were stained with CD3-PE-Cy7, CD8-PerCP, CD4-APC-Cy7, CD161-APC specific mAbs; as well as the anti-Vα7.2-FITC mAb D5 (generated in-house; human MAIT cells utilize the Vα7.2 alpha chain) and PE-labeled tetramers of mouse MR1-β2m-acetyl-6-Formyl Pterin (mouse MR1 had been refolded with either 6-formyl pterin or acetyl-6-formyl pterin). 10-20% of D5-positive, CD161-positive cells stained with tetramers of mouse MR1-β2m-acetyl-6-Formyl Pterin, depending on source of patient PBMCs.

MR1-Restricted MAIT Activation

While 6-FP was shown to be a ligand for MR1, it did not activate MAIT cells or Jurkat cells transfected with a MAIT TCR. However, C1R cells infected with *Salmonella typhimurium* activated Jurkat cells transduced with a MAIT TCR (Jurkat.MAIT). Subsequently, a fraction present only in the supernatant of *Salmonella* grown in M9 minimal media (i.e. lacking vitamin supplements), but not in control M9 media in the absence of *Salmonella*, that enabled the refolding of MR1 analogous to that of MR1-6FP was isolated and identified. High accuracy ESI TOF mass spectrometry allowed accurate determination of the mass-to-charge (m/z) ratio (329.1094) of this MR1-ligated compound, which in turn allowed a tentative atomic composition of $C_{12}H_{18}N_4O_7$. A search for a potential matching compound suggested a known bi-product of riboflavin (vitamin B2) biosynthesis in bacteria, namely 7-hydroxy-6-methyl-8-ribityl-lumazine (RL-6-ME,7OH) ($C_{12}H_{16}N_4O_7$). Accordingly, the mass spectrometry data was consistent with the reduced form of RL-6-ME,7OH representing a MAIT cell activating ligand. The structure of RL-6-ME,7OH is closely related to 6-FP, but possesses an additional ribityl moiety that, based on the crystal structure of MR1-6FP, would potentially permit direct contact by the MAIT TCR. RL-6-ME,7OH and its precursor, 6,7-dimethyl-8-ribityl lumazine (RL-6,7-DiMe) are both derived from the riboflavin pathway present in most, but not all bacteria and yeast.

Next, to formally establish whether 7-hydroxy-6-methyl-8-ribityl lumazine and/or its precursor, 6,7-dimethyl-8-ribityl lumazine, could activate MAIT cells, both compounds were chemically synthesized their ability to enable MR1 refolding and to activate Jurkat.MAIT cells and human MAIT cells from peripheral blood tested. Both compounds could be refolded with MR1, whereas riboflavin itself did not form MR1-β2m complexes. Both compounds failed to activate the control Jurkat.LC13 line in the presence of C1R.HLA-B8 cells, yet both compounds activated Jurkat.MAIT cells in the presence of C1R cells expressing MR1, whereas riboflavin did not. Moreover, both compounds specifically activated MAIT cells, as judged by CD69 upregulation and intracellular cytokine staining for IFN-γ and TNF-α. Thus, direct precursors of riboflavin biosynthesis activate MAIT cells. Notably, the enzymatic pathway that generates these precursors are only found in microbes that are capable of activating MAIT cells and are absent on non-activating microbes (Table 4).

Example 5

Mouse Wild-Type MR1 (BirA Peptide-Tagged) Tetramers Refolded with Acetyl-6-Formyl Pterin Tetramers produced from mouse MR1 (BirA peptide-tagged; refolded with either 6-FP or acetyl-6-FP) can stain a proportion of human PBMC MAIT cells. Control tetramers made from human wild-type MR1 refolded with 6-FP or acetyl-6-FP fail to stain human MAIT cells, demonstrating xeno-reactivity of human MAIT cells towards mouse MR1 (Huang et al. PNAS, 2009).

Example 6

Mutant Human Leucine151Alamine MR1 (BirA Peptide-Tagged) Tetramers Refolded with 6-Formyl Pterin, or Acetyl-6-Formyl Pterin Tetramers produced from human Leucine151Alanine MR1 (BirA peptide-tagged; refolded with either 6-FP or acetyl-6-FP) were demonstrated to stain a proportion of human PBMC MAIT cells.

Example 7

Human MR1-Lys43Ala MR1 (C-Terminal Cysteine-Tagged) Tetramers Loaded with rRL-6-$CH_2OH$ For efficient production of MR1 tetramers with the potent stimulating ligand rRL-6-$CH_2OH$, mutant MR1 containing a Lysine-43-Alanine mutation (Lys43Ala-MR1, and containing a C-terminal cysteine) is first refolded (in the absence of a ligand: "empty", but otherwise using the standard refolding conditions described above, and then purified using the standard methods described previously. Refolded and purified empty Lys43Ala-MR1 can subsequently be loaded with rRL-6-$CH_2OH$ in the following manner: empty Lys43Ala-MR1 is incubated in the presence of 130× molar excess of rRL-6-$CH_2OH$ for 4 hours at room temperature in the dark. Lys43Ala-MR1 thus loaded with rRL-6-$CH_2OH$ is then reduced for 15 minutes by the addition of DTT to 5 mM final concentration, following which excess rRL-6-$CH_2OH$ and DTT is removed by passage over a PD-10 column (GE Healthcare) in PBS, and concentrated in a VIVASPIN 6 (Sartorius) centrifugal concentrator to 200 ul. Lys43Ala-MR1 thus loaded with rRL-6-$CH_2OH$ is then biotinylated with Maleimide-PEG2 biotin (Thermoscientific) at a 30:1 molar excess of biotin:protein at 4° C. in the dark overnight. Excess biotin is removed by passing biotinylated protein through an S200 10/300 GL (Healthcare) gel filtration column in Tris buffered saline (pH 8.0), prior to formation of tetramers by addition to PE Streptavidin (#554061, BD Pharmingen). Lys43Ala-MR1 loaded with rRL-6-$CH_2OH$ is capable of complexation with soluble MAIT TCR, and can be separated from both monomeric MAIT TCR and unloaded, empty Lys43Ala-MR1, thus demonstrating its functionality. Subsequent analysis by ESI-TOF mass spectrometry demonstrated the presence of rRL-6-$CH_2OH$ in Lys43Ala-MR1 complexed with MAIT TCR. Staining of human PBMCs with rRL-6-$CH_2OH$-loaded Lys43Ala-MR1 tetramers identify a CD161-positive, D5-positive (D5 is a TRAV1-2 specific mAb) population. Subsequent single-cell sorting of tetramer-positive PBMCs by flow cytometry, followed by TCR repertoire analysis using multiplex nested RT-PCR for simultaneous detection of variable α and β chains, demonstrated the use of the published invariant MAIT TRAV1-2-TRAJ33 alpha chain by tetramer-positive cells. Additionally, novel re-arranged TRAV1-2-TRAJ12 and TRAV1-2-TRAJ20 alpha chains have been detected in tetramer-positive PBMCs. There is a skewing of TCR beta chain repertoire towards TRBV6 and TRBV20 usage (Table 5), as reported previously (Tilloy et al, JEM, 1999).

Example 8

Mouse MR1-Lys43Ala MR1 (C-Terminal Cysteine-Tagged) Tetramers Loaded with rRL-6-$CH_2OH$ Mutant mouse MR1 containing a Lysine-43-Alanine mutation (Lys43Ala-MR1, and containing a C-terminal cysteine) can be refolded (in the absence of a ligand: "empty"), and can then be purified in the manner described above for mutant human Lysine43Alanine MR1. Similarly, refolded and purified empty mouse Lys43Ala-MR1 can then be loaded with rRL-6-$CH_2OH$, can be biotinylated and can be conjugated to PE-streptavidin to form tetramers. Staining of human PBMCs with rRL-6-$CH_2OH$-loaded mouse Lys43Ala-MR1 identify a CD161-positive, D5-positive population (D5 is a TRAV1-2 specific mAb).

Example 9

Wild-Type MR1 (C-Terminal Cysteine-Tagged) Refolded with rRL-6-$CH_2OH$ or rRL-7-OH (From Precursor Compounds 5-Amino-6-D-Ribitylamino-Uracil and Pyruvaldehyde; or 5-Amino-6-D-Ribitylamino-Uracil and Glycolaldehyde Respectively)

Wild-type human MR1 containing a C-terminal cysteine can be refolded with the addition of 5-amino-6-D-ribitylamino-uracil and pyruvaldehyde, using the standard refolding conditions described above, and then purified using the standard methods also described above. MR1 refolded in this way has rRL-6-$CH_2OH$ bound as determined by X-ray crystallography structural studies, and by electrospray ionization time-of-flight (ESI TOF) mass spectrometry. To produce tetramers, this MR1-rRL-6-$CH_2OH$ is reduced for 15 minutes by the addition of DTT to 5 mM final concentration, following which excess DTT is removed by passage over a PD-10 column (GE Healthcare) in PBS, and concentrated in a VIVASPIN 6 (Sartorius) centrifugal concentrator to 200 ul. MR1-rRL-6-$CH_2OH$ is then biotinylated with Maleimide-PEG2 biotin (Thermoscientific) at a 30:1 molar excess of biotin:protein at 4° C. in the dark overnight. Excess biotin is removed by passing biotinylated protein through an S200 10/300 GL (Healthcare) gel filtration column in Tris buffered saline (pH 8.0), prior to formation of tetramers by addition to PE Streptavidin (#554061, BD Pharmingen). MR1-rRL-6-$CH_2OH$ is capable of complexation with soluble MAIT TCR, and can be separated from excess monomeric MAIT TCR and binary MR1-rRL-6-$CH_2OH$, thus demonstrating its specificity. Additionally, specificity of MAIT TCR recognition of MR1-rRL-6-$CH_2OH$ was shown by surface plasmon resonance (SPR), where a soluble MAIT TCR (utilizing a TRBV6-1 beta chain) bound to MR1-rRL-6-$CH_2OH$ with a Kd value of 1.65 μM (Table 5). Analysis by ESI-TOF mass spectrometry demonstrates the presence of rRL-6-$CH_2OH$ in both binary MR1-rRL-6-$CH_2OH$, as well as MR1-rRL-6-$CH_2OH$ complexed with MAIT TCR. In the same manner human MR1 containing a C-terminal cysteine can be refolded with the addition of 5-amino-6-D-ribitylamino-uracil, and subsequently purified by fast protein liquid chromatography (FPLC) to yield MR1 refolded with a novel ribityllumazine metabolite, reduced 7-hydroxy-ribityllumazine (rRL-7-OH). The identity of rRL-7-OH bound to MR1 was confirmed by ESI TOF mass spectrometry, and by determining its structure using X-ray crystallography. The identity of rRL-7-OH bound to MR1 was also confirmed by refolding wild-type MR1 with 5-amino-6-D-ribitylamino-uracil and $^{13}C$-glycolaldehyde to yield MR1-$^{13}C$-rRL-7-OH. Staining of human PBMCs with MR-rRL-7-OH tetramers identify the same CD161-positive population as was identified by staining with the K43A-MR1-rRL-6-$CH_2OH$ tetramer. Similarly, comparable staining of a Jurkat-MAIT-TRBV6-1 cell line with human MR1-rRL-6-$CH_2OH$ and human MR1-rRL-7-OH tetramers has been demonstrated. In addition, tetramers have been prepared from mouse wild-type MR1-rRL-6-$CH_2OH$ (containing a C-terminal cysteine), refolded and purified using 5-amino-6-D-ribitylamino-uracil and pyruvaldehyde. These mouse MR1-rRL-6-$CH_2OH$ tetramers stain MAIT TCR-BW hybridomas (prepared from the fusion of mouse Vα19iTG splenocytes with the BW cell line), but not control BW cells, demonstrating their specificity in binding to mouse MAIT TCRs.

TABLE 2

| Composition of RPMI medium: Vitamins are highlighted. | |
|---|---|
| RPMI-1640 Medium Component | R0883 [1x] g/L |
| Inorganic Salts | |
| Calcium Nitrate•$4H_2O$ | 0.1 |
| Magnesium Sulfate (anhydrous) | 0.04884 |
| Potassium Chloride | 0.4 |
| Sodium Bicarbonate | 2 |
| Sodium Chloride | 6 |
| Sodium Phosphate Dibasic (anhydrous) | 0.8 |
| Amino Acids | |
| L-Alanyl-L-Glutamine | — |
| L-Arginine | 0.2 |
| L-Asparagine (anhydrous) | 0.05 |
| L-Aspartic Acid | 0.02 |
| L-Cystine•2HCl | 0.0652 |
| L-Glutamic Acid | 0.02 |
| L-Glutamine | — |
| Glycine | 0.01 |
| L-Histidine | 0.015 |
| Hydroxy-L-Proline | 0.02 |
| L-Isoleucine | 0.05 |
| L-Leucine | 0.05 |
| L-Lysine•HCl | 0.04 |
| L-Methionine | 0.015 |
| L-Phenylalanine | 0.015 |
| L-Proline | 0.02 |
| L-Serine | 0.03 |
| L-Threonine | 0.02 |
| L-Tryptophan | 0.005 |
| L-Tyrosine•2Na•$2H_2O$ | 0.02883 |
| L-Valine | 0.02 |
| Vitamins | |
| D-Biotin | 0.0002 |
| Choline Chloride | 0.003 |
| Folic Acid | 0.001 |
| myo-Inositol | 0.035 |
| Niacinamide | 0.001 |
| p-Aminobenzoic Acid | 0.001 |
| D-Pantothenic Acid (hemicalcium) | 0.00025 |
| Pyridoxine•HCl | 0.001 |
| Riboflavin | 0.0002 |
| Thiamine•HCl | 0.001 |
| Vitamin $B_{12}$ | 0.000005 |
| Other | |
| D-Glucose | 2 |
| Glutathione (reduced) | 0.001 |
| Phenol Red•Na | 0.0053 |
| Add | |
| L-Glutamine | 0.3 |
| Sodium Bicarbonate | — |

TABLE 3

| Data collection and refinement statistics. | |
|---|---|
| | MR1 |
| Data collection | |
| Temperature | 100 K |
| Resolution limits (Å) | 89.78-3.2 (3.37-3.2) |
| Space Group | $P2_12_12_1$ |
| Cell dimensions (Å) | a = 59.15, b = 89.78, c = 171.34, $\alpha = \gamma = \beta = 90.00°$ |
| Total N° observations | 51923 |
| N° unique observations | 15374 |
| Multiplicity | 3.4 (3.4) |

TABLE 3-continued

| Data collection and refinement statistics. | |
|---|---|
| | MR1 |
| Data completeness | 98.1 (95.7) |
| $I/\sigma_1$ | 4.5 (1.8) |
| $R_{p.i.m}{}^1$ (%) | 16.6 (42.5) |
| Refinement statistics | |
| $R_{factor}{}^2$ (%) | 19.3 |
| $R_{free}{}^3$ (%) | 25.8 |
| Non hydrogen atoms | |
| Protein | 5961 |
| 6-formyl pterin | 28 |
| Phosphate ion | 5 |
| Water | 1 |
| Ramachandran plot (%) | |
| Most favoured | 95 |
| Outliers | 0.1 |
| B-factors ($Å^2$) | |
| Average main chain | 36.7 |
| Average side chain | 46.2 |
| 6-formyl pterin | 51.3 |
| rmsd bonds (Å) | 0.010 |
| rmsd angles (°) | 1.16 |

[1] $R_{p.i.m} = \Sigma_{hkl}[1/(N-1)]^{1/2} \Sigma_i|I_{hkl,i} - \langle I_{hkl}\rangle|/\Sigma_{hkl} \langle I_{hkl}\rangle$

[2] $R_{factor} = (\Sigma||F_o| - |F_c||)/(\Sigma|F_o|)$ - for all data except as indicated in footnote 3.

[3] 5% of data was used for the $R_{free}$ calculation

Values in parentheses refer to the highest resolution bin.

TABLE 4

| Contracts between MR1 and 6-formyl-pterin. | | |
|---|---|---|
| 6-formyl Pterin | MR1 | Bond |
| C7 | $Lys43^{NZ}$ | Covalent link |
| | $Lys43^{CD}$ | |
| | $Lys43^{CE}$ | VDW |
| | $Tyr7^{CD1}$ | VDW |
| | $Tyr7^{CE1}$ | VDW |
| | $Tyr7^{CZ}$ | VDW |
| C5 | $Lys43^{NZ}$ | VDW |
| | $Tyr7^{CD1}$ | VDW |
| | $Tyr7^{CE1}$ | VDW |
| | $Tyr7^{CZ}$ | VDW |
| N4 | $Trp69^{CZ3}$ | VDW |
| | $Lys43^{NZ}$ | VDW |
| | $Tyr7^{CG}$ | VDW |
| | $Tyr7^{CD1}$ | VDW |
| C1 | $Trp69^{CZ3}$ | VDW |
| C4 | $Arg9^{NH2}$ | VDW |
| | $Trp69^{CZ3}$ | VDW |
| | $Arg94^{NH1}$ | VDW |
| | $Ile96^{CD1}$ | VDW |
| O4 | $Arg9^{NH3}$ | VDW |
| | $Trp69^{CZ3}$ | VDW |
| | $Arg94^{NH1}$ | VDW |
| | $Arg9^{NE}$ | VDW |
| | $Arg9^{CZ}$ | VDW |
| N2 | $Arg9^{NH3}$ | VDW |
| | $Arg94^{NH1}$ | H-bond |
| | $Ile96^{CG1}$ | VDW |
| | $Ile96^{CD1}$ | VDW |
| C3 | $Ile96^{CD1}$ | VDW |
| N6 | $Gln153^{OE1}$ | VDW |
| N1 | $Trp156^{CE2}$ | VDW |
| | $Trp156^{NE1}$ | VDW |
| N3 | $Tyr62^{CZ}$ | VDW |
| | $Tyr62^{CE1}$ | VDW |

TABLE 4-continued

| Contracts between MR1 and 6-formyl-pterin. | | |
|---|---|---|
| 6-formyl Pterin | MR1 | Bond |
| C6 | Tyr62$^{CZ}$ | VDW |
| | Lys43$^{NZ}$ | VDW |
| | Tyr62$^{CD1}$ | VDW |
| | Tyr62$^{CE1}$ | VDW |
| | Tyr7$^{CE2}$ | VDW |
| | Tyr7$^{CZ}$ | |

* Atomic contacts determined using the CCP4i implementation of CONTACT and a cutoff of 4.0 Å for vdw interactions and 3.3 Å for h-bond interactions.

TABLE 5

TCR gene usage by MAIT cells isolated from single cell sorting using MR1-rRl-6-$CH_2OH$ tetramers

| | Donor ID All TRAV 1-2 | | | |
|---|---|---|---|---|
| | 1 | 2 | 3 | 4 |
| TRAJ33*01 | 24 | 11 | 38 | 32 |
| TRAJ20*01 | 5 | 1 | 3 | 1 |
| TRAJ12*01 | 2 | 1 | 2 | 2 |
| Total | 32 | 13 | 43 | 35 |

| | Donor ID | | | |
|---|---|---|---|---|
| | 1 | 2 | 3 | 4 |
| TRBV6-4 | 15 | 7 | 11 | 14 |
| TRBV20 | 1 | 3 | 13 | 3 |
| TRBV24 | 2 | 2 | 0 | 1 |
| TRBV15 | 2 | 0 | 0 | 3 |
| TRBV19 | 2 | 0 | 0 | 0 |
| TRBV10 | 1 | 0 | 0 | 0 |
| TRBV4-2 | 0 | 0 | 1 | 0 |
| Total | 23 | 12 | 25 | 21 |

Table of flow cytometric single-cell sorted PBMCs from 4 healthy patients (stained and gated on CD3+, CD4−, CD161+, human Lys43Ala-rRL-6-$CH_2OH$ tetramer+ cells) showing exclusive TRAV1-2 usage, and predominant TRAJ33*01 segment usage, with novel TRAJ20*01 and TRAJ12*01 segment usage (left panel). Beta chains utilized include: TRBV6-4, TRABV20, TRBV24, TRBV15, TRBV19, TRBV10, TRBV4-2 (right panel).

TABLE 6

Wild-type MR1-rRL-7-OH binds to MAIT TCR (TRBV6-1) as shown by Surface Plasmon Resonance (SPR)

| TCR | MR1-6-FP (μM) | MR1-rRL-7-OH (μM) |
|---|---|---|
| 6-1 | >300 | 5.64 ± 0.40 |
| 6-1$^{Y95F}$ | N.B | 48.17 ± 3.60 |

Table of MR1-rRL-7-OH binds to MAIT TCRs. Surface Plasmon Resonance (SPR) studies of MR1-rRL-7-OH interaction with wild-type MAIT TCR (utilizing TRBV6-1; 6-1; top row; Kd 5.64 μM) or mutant Y95F MAIT TCR (α-chain Y95F mutation; 6-1$^{Y95F}$; bottom panel; Kd 48.17 μM). Shown are dissociation constant ($K_d$) values in μM; $K_d$ values for the negative control MR1-6-FP are also indicated.

BIBLIOGRAPHY

1. Downward, (2000) *J Mass Spectrom*. April; 35 (4): 493-503.
2. Ehring H, (1999) *Analytical Biochemistry*, Vol. 267 (2) pp. 252-259.
3. Engen, J. R. and Smith, D. L. (2001) *Anal. Chem.* 73, 256A-265A.
4. Ernst Schering (2004) *Res Found Workshop* (44): 149-67.
5. Godfrey, D. I., J. Rossjohn, and J. McCluskey. (2010b) Fighting infection with your MAITs. *Nat Immunol* 11:693-695.
6. Gold, M. C., S. Cerri, S. Smyk-Pearson, M. E. Cansler, T. M. Vogt, J. Delepine, E. Winata, G. M. Swarbrick, W.-J. Chua, Y. Y. L. Yu, O. Lantz, M. S. Cook, M. D. Null, D. B. Jacoby, M. J. Harriff, D. A. Lewinsohn, T. H. Hansen, and D. M. Lewinsohn. (2010) Human Mucosal Associated Invariant T Cells Detect Bacterially Infected Cells. *PLoS Biol* 8:e1000407.
7. Gold, M. C., S. Cerri, S. Smyk-Pearson, M. E. Cansler, T. M. Vogt, J. Delepine, E. Winata, G. M. Swarbrick, W.-J. Chua, Y. Y. L. Yu, O. Lantz, M. S. Cook, M. D. Null, D. B. Jacoby, M. J. Harriff, D. A. Lewinsohn, T. H. Hansen, and D. M. Lewinsohn. (2010a) Human Mucosal Associated Invariant T Cells Detect Bacterially Infected Cells. *PLoS Biol* 8:e1000407.
8. Gold, M. C., S. Cerri, S. Smyk-Pearson, M. E. Cansler, T. M. Vogt, J. Delepine, E. Winata, G. M. Swarbrick, W. J. Chua, Y. Y. Yu, O. Lantz, M. S. Cook, M. D. Null, D. B. Jacoby, M. J. Harriff, D. A. Lewinsohn, T. H. Hansen, and D. M. Lewinsohn. (2010b) Human mucosal associated invariant T cells detect bacterially infected cells. *PLoS Biol* 8:e1000407.
9. Huang et al (1998) *Journal of Molecular Biology*, Vol. 281 (1) pp. 61-67.
10. Huang, S., S. Gilfillan, M. Cella, M. J. Miley, O. Lantz, L. Lybarger, D. H. Fremont, and T. H. Hansen. (2005) Evidence for MR1 Antigen Presentation to Mucosal-associated Invariant T Cells. *Journal of Biological Chemistry* 280:21183-21193.
11. Huang, S., S. Gilfillan, S. Kim, B. Thompson, X. Wang, A. J. Sant, D. H. Fremont, O. Lantz, and T. H. Hansen. (2008) MR1 uses an endocytic pathway to activate mucosal-associated invariant T cells. *J Exp Med* 205: 1201-1211.
12. Huang, S., E. Martin, S. Kim, L. Yu, C. Soudais, D. H. Fremont, O. Lantz, and T. H. Hansen. (2009) MR1 antigen presentation to mucosal-associated invariant T cells was highly conserved in evolution. *Proc Natl Acad Sci USA* 106:8290-8295.
13. Kawachi, I., J. Maldonado, C. Strader, and S. Gilfillan. (2006). MR1-Restricted VCE±19i Mucosal Associated Invariant T Cells Are Innate T Cells in the Gut Lamina Propria That Provide a Rapid and Diverse Cytokine Response. *The Journal of Immunology* 176:1618-1627.
14. Kiselar and Downard, (1999) *Anal Chem*. May 1; 71 (9): 1792-801.
15. Lantz and Bendelac. (1994) *J. Exp Med.* 180:1097-106;
16. Le Bourhis, L., E. Martin, I. Peguillet, A. Guihot, N. Froux, M. Core, E. Levy, M. Dusseaux, V. Meyssonnier, V. Premel, C. Ngo, B. Riteau, L. Duban, D. Robert, S. Huang, M. Rottman, C. Soudais, and O. Lantz. (2010) Antimicrobial activity of mucosal-associated invariant T cells. *Nat Immunol* 11:701-708.
17. Le Bourhis, L., L. Guerri, M. Dusseaux, E. Martin, C. Soudais, and O. Lantz. (2011) Mucosalassociated invariant T cells: unconventional development and function. *Trends in Immunology* 32:212-218.
18. Lybarger (2003)
19. Manca, Ann (1991) 1*st Super Sanita.* 27: 15-9.
20. Martin, E., E. Treiner, L. Duban, L. Guerri, H. Laude, C. Toly, V. Premel, A. Devys, I. C. Moura, F. Tilloy, S. Cherif, G. Vera, S. Latour, C. Soudais, and O. Lantz. (2009) Stepwise Development of MAIT Cells in Mouse and Human. *PLoS Biol* 7:e54.
21. Miyazaki Y, Miyake S, Chiba A, Lantz O, Yamamura T. (2011) Mucosal-associated invariant T cells regulate Th1 response in multiple sclerosis, *In Immunol;* 23(9):529-35.

22. Peterfalvi A, Gomori E, Magyarlaki T, Pal J, Banati M, Javorhazy A, Szekeres-Bartho J, Szereday L, Ines Z, (2008). Invariant Valpha7.2-Jalpha33 TCR is expressed in human kidney and brain tumors indicating infiltration by mucosal-associated invariant T (MAIT) cells. *Int Immunol.* 20(12):1517-25.
23. Riegert P, Wanner V, Bahram S., (1998). Genomics, isoforms, expression and logeny of the MHC classI-related MR1 gene. *J Immunol* 161(8):4066-77.
24. Reantragoon R, Kjer-Nielsen L, Patel O, Chen Z, Tiling P T, Bhati M, Kostenko L, Bharadwaj M, Meehan B, Hansen T H, Godfrey D I, Rossjohn J, McCluskey J. (2012) Structural insight into MR1-mediated recognition of the mucosal associated invariant T cell receptor. *J Exp Med.* 209(4):761-74
25. Saito and Patterson (1996) *Methods*. June; 9 (3): 516-24.
26. Shimamura, M., Huang, Y. Y., Okamoto, N., Suzuki, N., Yasuoka, J., Morita, K., Nishiyama, A., Amano, Y., and Mishina, T. (2007) Modulation of Va19 NKT cell immune responses by a-mannosyl ceramide derivatives consisting of a series of modified sphingosines. *Eur. J. Immunol.* 37, 1836-1844.
27. Tilloy, F., E. Treiner, S.-H. Park, C. Garcia, F. o. Lemonnier, H. de la Salle, A. Bendelac, M. Bonneville, and O. Lantz. (1999) An Invariant T Cell Receptor CE±Chain Defines a Novel TAP-independent Major Histocompatibility Complex Class Ib,Äìrestricted CE±/CE<T Cell Subpopulation in Mammals. *The Journal of Experimental Medicine* 189:1907-1921.
28. Treiner et al. (2005) Microbes Infect. 7(3):552-9.
29. Treiner, E., L. Duban, S. Bahram, M. Radosavljevic, V. Wanner, F. Tilloy, P. Affaticati, S. Gilfillan, and O. Lantz. (2003) Selection of evolutionarily conserved mucosal-associated invariant T cells by MR1. *Nature* 422:164-169.
30. Zinkernagel and Doherty, (1997).
31. Altman et al., "Formation of functional peptide complexes of class II major histocompatibility complex proteins from subunits produced in *Escherichia coli,*" *Proc. Natl. Acad. Sci. USA*, pp. 10330-10334, November 1993, vol. 90.
32. Garboczi et al., "HLA-A2.peptide complexes: Refolding and crystallization of molecules expressed in *Escherichia coli* and complexed with single antigenic peptides," *Proc. Natl. Acad. Sci.,* 89:3429-3433, 1992.f

The invention claimed is:

1. A method of detecting the presence of MAIT cells in a biological sample from a subject, the method comprising the steps of a) contacting the biological sample with antigen presenting cells expressing MR1 bound to a ligand or a soluble form of MR1 bound to a ligand, under conditions that would allow binding of the MR1 or the soluble form of MR1 with MATT cells present in the sample, wherein the ligand is a compound selected from the group consisting of rRL-6HM, rRL-6AM, RL-6M, RP-5PA, 6-formyl pterin, acetyl 6-formyl pterin, 6-methyl-7-hydroxy-8-ribityl lumazine, and 6-,7-dimethyl-8-Ribityl Lumazine; and b) detecting the presence of MAIT cell bound MR1 or MAIT cell bound soluble form of MR1 in the biological sample, thereby detecting the presence of MAIT cells in a biological sample from a subject.

2. The method according to claim 1, wherein the ligand is rRL-6HM.

3. The method of claim 1, wherein the biological sample is a biological fluid.

4. The method of claim 1, wherein the biological sample is a cell sample.

5. The method of claim 1, wherein the biological sample is a tissue sample.

6. The method of claim 3, wherein the biological fluid is serum, lymph, or blood.

7. The method of claim 5, wherein the tissue sample is a bone marrow or a tissue biopsy sample including mucosal tissue.

8. The method of claim 7, wherein the tissue biopsy sample is from the gut, gut lamina propria, or lungs.

9. The method of claim 1, wherein the MR1 is a human, primate, or mouse MR1 polypeptide.

10. The method of claim 8, wherein the MR1 polypeptide comprises SEQ ID NO: 1 or SEQ ID NO: 4.

11. The method of claim 1, wherein the subject is a human.

* * * * *

SEQUENCE LISTING

```
<160> NUMBER OF SEQ ID NOS: 6

<210> SEQ ID NO 1
<211> LENGTH: 341
<212> TYPE: PRT
<213> ORGANISM: homosapian

<400> SEQUENCE: 1

Met Gly Glu Leu Met Ala Phe Leu Leu Pro Leu Ile Ile Val Leu Met
1               5                   10                  15

Val Lys His Ser Asp Ser Arg Thr His Ser Leu Arg Tyr Phe Arg Leu
            20                  25                  30

Gly Val Ser Asp Pro Ile His Gly Val Pro Glu Phe Ile Ser Val Gly
        35                  40                  45

Tyr Val Asp Ser His Pro Ile Thr Thr Tyr Asp Ser Val Thr Arg Gln
    50                  55                  60

Lys Glu Pro Arg Ala Pro Trp Met Ala Glu Asn Leu Ala Pro Asp His
65                  70                  75                  80

Trp Glu Arg Tyr Thr Gln Leu Leu Arg Gly Trp Gln Gln Met Phe Lys
                85                  90                  95

Val Glu Leu Lys Arg Leu Gln Arg His Tyr Asn His Ser Gly Ser His
            100                 105                 110

Thr Tyr Gln Arg Met Ile Gly Cys Glu Leu Leu Glu Asp Gly Ser Thr
        115                 120                 125

Thr Gly Phe Leu Gln Tyr Ala Tyr Asp Gly Gln Asp Phe Leu Ile Phe
    130                 135                 140

Asn Lys Asp Thr Leu Ser Trp Leu Ala Val Asp Asn Val Ala His Thr
145                 150                 155                 160

Ile Lys Gln Ala Trp Glu Ala Asn Gln His Glu Leu Leu Tyr Gln Lys
                165                 170                 175

Asn Trp Leu Glu Glu Glu Cys Ile Ala Trp Leu Lys Arg Phe Leu Glu
            180                 185                 190

Tyr Gly Lys Asp Thr Leu Gln Arg Thr Glu Pro Pro Leu Val Arg Val
        195                 200                 205

Asn Arg Lys Glu Thr Phe Pro Gly Val Thr Ala Leu Phe Cys Lys Ala
    210                 215                 220
```

```
His Gly Phe Tyr Pro Pro Glu Ile Tyr Met Thr Trp Met Lys Asn Gly
225                 230                 235                 240

Glu Glu Ile Val Gln Glu Ile Asp Tyr Gly Asp Ile Leu Pro Ser Gly
                245                 250                 255

Asp Gly Thr Tyr Gln Ala Trp Ala Ser Ile Glu Leu Asp Pro Gln Ser
            260                 265                 270

Ser Asn Leu Tyr Ser Cys His Val Glu His Cys Gly Val His Met Val
        275                 280                 285

Leu Gln Val Pro Gln Glu Ser Glu Thr Ile Pro Leu Val Met Lys Ala
    290                 295                 300

Val Ser Gly Ser Ile Val Leu Val Ile Val Leu Ala Gly Val Gly Val
305                 310                 315                 320

Leu Val Trp Arg Arg Arg Pro Arg Glu Gln Asn Gly Ala Ile Tyr Leu
                325                 330                 335

Pro Thr Pro Asp Arg
            340


<210> SEQ ID NO 2
<211> LENGTH: 319
<212> TYPE: PRT
<213> ORGANISM: homosapian

<400> SEQUENCE: 2

Arg Thr His Ser Leu Arg Tyr Phe Arg Leu Gly Val Ser Asp Pro Ile
1               5                   10                  15

His Gly Val Pro Glu Phe Ile Ser Val Gly Tyr Val Asp Ser His Pro
            20                  25                  30

Ile Thr Thr Tyr Asp Ser Val Thr Arg Gln Lys Glu Pro Arg Ala Pro
        35                  40                  45

Trp Met Ala Glu Asn Leu Ala Pro Asp His Trp Glu Arg Tyr Thr Gln
    50                  55                  60

Leu Leu Arg Gly Trp Gln Gln Met Phe Lys Val Glu Leu Lys Arg Leu
65                  70                  75                  80

Gln Arg His Tyr Asn His Ser Gly Ser His Thr Tyr Gln Arg Met Ile
                85                  90                  95

Gly Cys Glu Leu Leu Glu Asp Gly Ser Thr Thr Gly Phe Leu Gln Tyr
            100                 105                 110

Ala Tyr Asp Gly Gln Asp Phe Leu Ile Phe Asn Lys Asp Thr Leu Ser
        115                 120                 125

Trp Leu Ala Val Asp Asn Val Ala His Thr Ile Lys Gln Ala Trp Glu
    130                 135                 140

Ala Asn Gln His Glu Leu Leu Tyr Gln Lys Asn Trp Leu Glu Glu Glu
145                 150                 155                 160

Cys Ile Ala Trp Leu Lys Arg Phe Leu Glu Tyr Gly Lys Asp Thr Leu
                165                 170                 175

Gln Arg Thr Glu Pro Pro Leu Val Arg Val Asn Arg Lys Glu Thr Phe
            180                 185                 190

Pro Gly Val Thr Ala Leu Phe Cys Lys Ala His Gly Phe Tyr Pro Pro
        195                 200                 205

Glu Ile Tyr Met Thr Trp Met Lys Asn Gly Glu Glu Ile Val Gln Glu
    210                 215                 220

Ile Asp Tyr Gly Asp Ile Leu Pro Ser Gly Asp Gly Thr Tyr Gln Ala
225                 230                 235                 240

Trp Ala Ser Ile Glu Leu Asp Pro Gln Ser Ser Asn Leu Tyr Ser Cys
```

```
                245                 250                 255

His Val Glu His Cys Gly Val His Met Val Leu Gln Val Pro Gln Glu
            260                 265                 270

Ser Glu Thr Ile Pro Leu Val Met Lys Ala Val Ser Gly Ser Ile Val
        275                 280                 285

Leu Val Ile Val Leu Ala Gly Val Gly Val Leu Val Trp Arg Arg Arg
    290                 295                 300

Pro Arg Glu Gln Asn Gly Ala Ile Tyr Leu Pro Thr Pro Asp Arg
305                 310                 315


<210> SEQ ID NO 3
<211> LENGTH: 22
<212> TYPE: PRT
<213> ORGANISM: homosapian

<400> SEQUENCE: 3

Met Gly Glu Leu Met Ala Phe Leu Leu Pro Leu Ile Ile Val Leu Met
1               5                   10                  15

Val Lys His Ser Asp Ser
            20


<210> SEQ ID NO 4
<211> LENGTH: 341
<212> TYPE: PRT
<213> ORGANISM: mus musculus

<400> SEQUENCE: 4

Met Met Leu Leu Leu Pro Leu Leu Ala Val Phe Leu Val Lys Arg Ser
1               5                   10                  15

His Thr Arg Thr His Ser Leu Arg Tyr Phe Arg Leu Ala Val Ser Asp
            20                  25                  30

Pro Gly Pro Val Val Pro Glu Phe Ile Ser Val Gly Tyr Val Asp Ser
        35                  40                  45

His Pro Ile Thr Thr Tyr Asp Ser Val Thr Arg Gln Lys Glu Pro Lys
    50                  55                  60

Ala Pro Trp Met Ala Glu Asn Leu Ala Pro Asp His Trp Glu Arg Tyr
65                  70                  75                  80

Thr Gln Leu Leu Arg Gly Trp Gln Gln Thr Phe Lys Ala Glu Leu Arg
                85                  90                  95

His Leu Gln Arg His Tyr Asn His Ser Gly Leu His Thr Tyr Gln Arg
            100                 105                 110

Met Ile Gly Cys Glu Leu Leu Glu Asp Gly Ser Thr Thr Gly Phe Leu
        115                 120                 125

Gln Tyr Ala Tyr Asp Gly Gln Asp Phe Ile Ile Phe Asn Lys Asp Thr
    130                 135                 140

Leu Ser Trp Leu Ala Met Asp Tyr Val Ala His Ile Thr Lys Gln Ala
145                 150                 155                 160

Trp Glu Ala Asn Leu His Glu Leu Gln Tyr Gln Lys Asn Trp Leu Glu
                165                 170                 175

Glu Glu Cys Ile Ala Trp Leu Lys Arg Phe Leu Glu Tyr Gly Arg Asp
            180                 185                 190

Thr Leu Glu Arg Thr Glu His Pro Val Val Arg Thr Thr Arg Lys Glu
        195                 200                 205

Thr Phe Pro Gly Ile Thr Thr Phe Phe Cys Arg Ala His Gly Phe Tyr
    210                 215                 220

Pro Pro Glu Ile Ser Met Thr Trp Met Lys Asn Gly Glu Glu Ile Ala
```

```
225                 230                 235                 240

Gln Glu Val Asp Tyr Gly Gly Val Leu Pro Ser Gly Asp Gly Thr Tyr
                245                 250                 255

Gln Thr Trp Leu Ser Val Asn Leu Asp Pro Gln Ser Asn Asp Val Tyr
            260                 265                 270

Ser Cys His Val Glu His Cys Gly Arg Gln Met Val Leu Glu Ala Pro
        275                 280                 285

Arg Glu Ser Gly Asp Ile Leu Arg Val Ser Thr Ile Ser Gly Thr Thr
    290                 295                 300

Ile Leu Ile Ile Ala Leu Ala Gly Val Gly Val Leu Ile Trp Arg Arg
305                 310                 315                 320

Ser Gln Glu Leu Lys Glu Val Met Tyr Gln Pro Thr Gln Val Asn Glu
                325                 330                 335

Gly Ser Ser Pro Ser
            340


<210> SEQ ID NO 5
<211> LENGTH: 322
<212> TYPE: PRT
<213> ORGANISM: murine

<400> SEQUENCE: 5

Arg Thr His Ser Leu Arg Tyr Phe Arg Leu Ala Val Ser Asp Pro Gly
1               5                   10                  15

Pro Val Val Pro Glu Phe Ile Ser Val Gly Tyr Val Asp Ser His Pro
            20                  25                  30

Ile Thr Thr Tyr Asp Ser Val Thr Arg Gln Lys Glu Pro Lys Ala Pro
        35                  40                  45

Trp Met Ala Glu Asn Leu Ala Pro Asp His Trp Glu Arg Tyr Thr Gln
    50                  55                  60

Leu Leu Arg Gly Trp Gln Gln Thr Phe Lys Ala Glu Leu Arg His Leu
65                  70                  75                  80

Gln Arg His Tyr Asn His Ser Gly Leu His Thr Tyr Gln Arg Met Ile
                85                  90                  95

Gly Cys Glu Leu Leu Glu Asp Gly Ser Thr Thr Gly Phe Leu Gln Tyr
            100                 105                 110

Ala Tyr Asp Gly Gln Asp Phe Ile Ile Phe Asn Lys Asp Thr Leu Ser
        115                 120                 125

Trp Leu Ala Met Asp Tyr Val Ala His Ile Thr Lys Gln Ala Trp Glu
    130                 135                 140

Ala Asn Leu His Glu Leu Gln Tyr Gln Lys Asn Trp Leu Glu Glu Glu
145                 150                 155                 160

Cys Ile Ala Trp Leu Lys Arg Phe Leu Glu Tyr Gly Arg Asp Thr Leu
                165                 170                 175

Glu Arg Thr Glu His Pro Val Val Arg Thr Thr Arg Lys Glu Thr Phe
            180                 185                 190

Pro Gly Ile Thr Thr Phe Phe Cys Arg Ala His Gly Phe Tyr Pro Pro
        195                 200                 205

Glu Ile Ser Met Thr Trp Met Lys Asn Gly Glu Glu Ile Ala Gln Glu
    210                 215                 220

Val Asp Tyr Gly Gly Val Leu Pro Ser Gly Asp Gly Thr Tyr Gln Thr
225                 230                 235                 240

Trp Leu Ser Val Asn Leu Asp Pro Gln Ser Asn Asp Val Tyr Ser Cys
                245                 250                 255
```

-continued

```
His Val Glu His Cys Gly Arg Gln Met Val Leu Glu Ala Pro Arg Glu
            260                 265                 270

Ser Gly Asp Ile Leu Arg Val Thr Ile Ser Gly Thr Thr Ile Leu Ile
        275                 280                 285

Ile Ala Leu Ala Gly Val Gly Val Leu Ile Trp Arg Arg Ser Gln Glu
    290                 295                 300

Leu Lys Glu Val Met Tyr Gln Pro Thr Gln Val Asn Glu Gly Ser Ser
305                 310                 315                 320

Pro Ser


<210> SEQ ID NO 6
<211> LENGTH: 18
<212> TYPE: PRT
<213> ORGANISM: murine

<400> SEQUENCE: 6

Met Met Leu Leu Leu Pro Leu Leu Ala Val Phe Leu Val Lys Arg Ser
1               5                   10                  15

His Thr
```

UNITED STATES PATENT AND TRADEMARK OFFICE
CERTIFICATE OF CORRECTION

PATENT NO. : 10,011,602 B2
APPLICATION NO. : 14/413164
DATED : July 3, 2018
INVENTOR(S) : Lars Kjer-Nielsen et al.

Page 1 of 1

It is certified that error appears in the above-identified patent and that said Letters Patent is hereby corrected as shown below:

On the Title Page

Item (72), please amend the named inventors:
"(72) Inventors: Lars Kjer-Nielsen, Carlton (AU);
James McCluskey, Carlton (AU);
Alexandra Corbett, Carlton (AU);
Jamie Rossjohn, Clayton (AU);
Patel Onisha, Clayton (AU);
David Paul Fairlie, Brisbane (AU);
Ligong Liu, Brisbane (AU)"

With:
-- (72) Inventors: Lars Kjer-Nielsen, Carlton (AU);
James McCluskey, Carlton (AU);
Alexandra Corbett, Carlton (AU);
Jamie Rossjohn, Clayton (AU);
Patel Onisha, Clayton (AU);
David Paul Fairlie, Brisbane (AU);
Ligong Liu, Brisbane (AU);
Sidonia Barbara Guiomar Eckle, Carlton (AU) --

Signed and Sealed this
Twenty-eighth Day of January, 2020

Andrei Iancu
*Director of the United States Patent and Trademark Office*